US006469036B1

(12) United States Patent
Costanzo et al.

(10) Patent No.: US 6,469,036 B1
(45) Date of Patent: *Oct. 22, 2002

(54) PEPTIDYL HETEROCYCLIC KETONES USEFUL AS TRYPTASE INHIBITORS

(75) Inventors: Michael J. Costanzo, Ivyland; Bruce E. Maryanoff, Forest Grove; Stephen C. Yabut, North Wales, all of PA (US)

(73) Assignee: Ortho-McNeil Pharmaceutical, Inc., Raritan, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/482,802

(22) Filed: Jan. 13, 2000

Related U.S. Application Data

(60) Provisional application No. 60/117,602, filed on Jan. 27, 1999.

(51) Int. Cl.[7] ............... A61K 31/40; A61K 31/403; A61K 31/404; C07D 207/16; C07D 209/42
(52) U.S. Cl. ............... 514/359; 514/361; 514/362; 514/363; 514/365; 514/367; 514/374; 514/375; 514/376; 514/397; 514/2; 514/19; 548/127; 548/180; 548/200; 548/214; 548/217; 548/236; 548/248; 548/255; 548/266.8; 548/306.1; 548/314.7; 548/361.1
(58) Field of Search ............... 548/127, 180, 548/200, 214, 217, 236, 248, 255, 266.8, 306.1, 314.7, 361.1; 514/359, 301, 362, 363, 365, 367, 372, 374, 375, 376, 397, 2, 19

(56) References Cited

U.S. PATENT DOCUMENTS

| 5,523,308 A | | 6/1996 | Costanzo et al. ........... 514/317 |
| 5,525,623 A | | 6/1996 | Spear et al. ................ 514/423 |
| 5,827,860 A | * | 10/1998 | Costanzo et al. ........... 514/369 |
| 5,827,866 A | * | 10/1998 | Costanzo et al. ........... 514/369 |

FOREIGN PATENT DOCUMENTS

| JP | 8-20597 | 1/1996 |
| WO | WO 96/19483 | 6/1996 |
| WO | WO 96/19491 | 6/1996 |
| WO | WO 96/30035 | 10/1996 |
| WO | WO 96/30396 | 10/1996 |
| WO | WO 96/37497 | 11/1996 |
| WO | WO 96/40741 | 12/1996 |
| WO | WO 96/40742 | 12/1996 |
| WO | WO 96/40744 | 12/1996 |
| WO | WO 97/17363 | 5/1997 |
| WO | WO 98/05333 | 2/1998 |
| WO | WO 98/09987 | 3/1998 |
| WO | WO 99/04752 | 2/1999 |
| WO | WO 99/26925 | 6/1999 |
| WO | WO 99/30729 | 6/1999 |

* cited by examiner

*Primary Examiner*—Richard L. Raymond
(74) *Attorney, Agent, or Firm*—Mary A. Appollina

(57) ABSTRACT

The present invention relates to a series of peptidyl heterocyclic ketones which are inflammatory cell serine protease inhibitors and their compositions and methods for the prevention and treatment of a variety of immunomediated inflammatory disorders. More particularly, these compounds are potent and selective inhibitors of tryptase and are therefore effective for the prevention and treatment of inflammatory diseases associated with the respiratory tract, such as asthma and allergic rhinitis.

24 Claims, No Drawings

PEPTIDYL HETEROCYCLIC KETONES USEFUL AS TRYPTASE INHIBITORS

CROSS-REFERENCE TO RELATED APPLICATION

This application claims priority from United States provisional application Serial No. 60/117,602, filed Jan. 27, 1999, the contents of which are hereby incorporated by reference.

FIELD OF THE INVENTION

This invention relates to a series of compounds which are peptidyl heterocyclic ketone inflammatory cell serine protease inhibitors and their compositions and methods for the prevention and treatment of a variety of immunomediated inflammatory disorders, skin hyperpigmentation, and trypsin mediated disorders. More particularly, these compounds are potent and selective inhibitors of tryptase and are therefore effective for the prevention and treatment of inflammatory diseases associated with the respiratory tract, such as asthma and allergic rhinitis, as well as other immunomediated inflammatory disorders, such as rheumatoid arthritis, conjunctivitis, psoriasis, inflammatory bowel disease, various vascular and dermatological conditions.

BACKGROUND OF THE INVENTION

Mast cells are a key cellular component of the inflammatory response and when activated, secrete numerous proinflammatory mediators, including histamine, arachidonic acid derivatives, and some serine proteases. Among these mast cell serine proteases is a unique carboxypeptidase, chymase and tryptase (Walls et al. *Eur. J. Pharmacol.* 1997, 328, 89–97). Active tryptase is a structurally unique trypsin-like serine protease which exists as a tetramer that is stabilized by heparin proteoglycans which are stored and secreted with the enzyme (Bode et al. *Nature* 1998, 392, 306–311). With the exception of neutrophil lactoferrin and possibly secretory leukocyte proteinase inhibitor, tryptase is generally not affected by endogenous serine protease inhibitors such as $\alpha_2$-macroglobin, $\alpha_2$-proteinase inhibitor, aprotinin, and antithrombin. It is postulated that in vivo tryptase activity may be regulated by the dissociation of the active tryptase tetramer into inactive monomers via the removal of heparin.

Tryptase is secreted exclusively by mast cells and comprises up to 25% of the total protein of the mast cell (Schwartz et al., *J. Clin. Invest.* 1989, 84, 1188–1195). Consequently, mast cell-derived tryptase is secreted in high concentrations at sites of tissue injury. Activated mast cells in atherosclerotic/restenotic plaque have been implicated in plaque rupture and stenosis and are also manifested in inflamed tissues of the gastrointestinal tract. Elevated tryptase levels have been detected in bronchoalveolar lavage fluid (asthma), tears (conjunctivitis), blister fluids (dermatitis), blood (anaphylaxis), cerebrospinal fluid (multiple sclerosis), synovial fluid (rheumatoid arthritis) (Rice et al. *Curr. Pharm. Design.* 1998, 4, 381–396). Elevated levels of tryptase have also been found in diseased arteries (atherosclerotic, restenotic) relative to normal arteries. Some cigarette smokers have elevated bronchooalveolar lavage fluid tryptase levels relative to nonsmokers, providing support for the hypothesis that mast cell proteases may contribute to lung destruction in smoker's emphysema (Kalenderian et al. *Chest* 1998, 94, 119–123).

The potent bronchodilating neuropeptides, vasoactive intestinal peptide (VIP) and peptide histidine methionine (PHM) are readily cleaved by tryptase in vitro whereas substance P, a potent bronchoconstricting peptide, is not (Drazen et al. *J. Clin. Invest* 1993, 91, 235–243). Tryptase has demonstrated the ability to generate bradykinin, which is known to induce bronchoconstriction in asthmatics (Zhang et al. *Mediators of Inflammation.* 1997, 6, 311–317). The ability of tryptase to stimulate inflammatory eosinophils and neutophil chemotaxis in vitro and in vivo is well known (Walls et al. *J. Immunol.* 1997, 159, 6216–6225). Inhaled tryptase has been shown to cause bronchoconstriction in sheep through the release of histamine (Abraham et al. *Amer. J. of Respir. and Crit. Care Med.* 1996, 154, 649–654). Its ability to directly stimulate mast cell degranulation in vitro and in animal models suggests that there may be a tryptase mediated amplification mechanism of the allergic inflammatory response (Walls et al. *Eur. J. Pharmacol.* 1997, 328, 89–97).

Currently, only trypsin and tryptase are known to activate the protease-activated receptor 2 (PAR-2), a cell surface G-protein-coupled receptor. The activation of PAR-2 is primarily associated with the induction of mitogenic response indicating that tryptase may have a role in pathological conditions associated with tissue hyperplasia, including the airway hyperplasia found in chronic asthmatics (Stone et al. *FEBS Letters* 1997, 417, 267–269). Tryptase also has multiple effects on fibroblasts and there is in vitro evidence to suggest that tryptase may involved in the early stages of fibrotic diseases, such as fibrotic lung disease, schieroderma, atherosclerosis, and cardiomyopathic disorders (Marone et al. *Circulation* 1998, 97, 971–978). Hence, an inhibitor of tryptase could provide a novel therapeutic approach for the prevention and treatment of a variety inflammatory diseases, such as vascular injury (atherosclerosis, restenosis), arthritis, inflammatory bowel disease, Crohn's disease, dermatitis, urticaria, bullous pemphigoid, psoriasis, schleroderma, fibrosis, conjunctivitis, allergic rhinitis, and particularly asthma.

Asthma is the most common chronic disease in developed countries. It is a complex disease involving multiple biochemical mediators for both its acute and chronic manifestations. Asthma is frequently characterized by the progressive development of hyperresponsiveness of the trachea and bronchi to both immunospecific allergens as well as generalized chemical or physical stimuli. The hyperresponsiveness of asthmatic bronchiolar tissue is postulated to result from chronic inflammation reactions, which irritate and damage the epithelium lining the airway wall and promote pathological thickening of the underlying tissue. Bronchial biopsy studies have indicated that even patients with mild asthma have features of inflammation in the airway wall. Mast cells have long been implicated in the pathogenesis of asthma, particularly in the acute response immediately after the exposure to allergen (Zhang et al. *Mediators of Inflammation* 1997, 6, 311–317).

The therapeutic strategy of employing tryptase inhibitors as a treatment for asthma in humans has been recently validated by the selective tryptase inhibitor, APC-366 (Tanaka et al. *Am. J. Respir. Crit. Care Med.* 1995, 152, 2076–2083). A recent Phase IIa study was conducted with 16 mild asthmatics who were dosed with either placebo or a nebulized dry powder formulation of APC-366 (Rice et al. Curr. Pharm. Design. 1998, 4, 381–396). Compared with placebo, the same subjects had a statistically significant improvement for the late airway response (33%; $\rho=0.012$) and a mean maximum decrease of forced expiratory volume in one second (21%; $\rho=0.007$) for late airway hyperresponsiveness. These positive results demonstrate that tryptase inhibition is a promising approach for the treatment of asthma in humans.

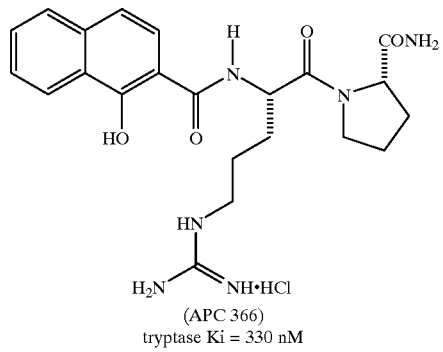

(APC 366)
tryptase Ki = 330 nM

Currently, the most effect therapy for chronic asthma involves treatment with glucocorticoids (Barnes *New Engl. J. Med.* 1995, 332, 868–875). However, glucocorticoid administration also generates a litany of local and systemic side-effects. Because of the limitations of glucocorticoids, there is an unmet medical need for improved asthma therapy. In contrast to drugs such as steroids that elicit multiple actions, tryptase inhibitors may elicit fewer side-effects through the selective inhibition of a specific inflammatory mediator (tryptase) that is exclusive to mast cells. Hence, tryptase inhibitors may offer similar efficacy in the treatment of asthma as the glucocorticoids without the same undesirable systemic side-effects.

Skin coloring has been of concern to human beings for many years. In particular, the ability to remove hyperpigmentation, such as found in age spots, freckles or aging skin generally, is of interest to individuals desiring a uniform complexion. There are also hyperpigmentation disorders that are desirable to treat. The compounds of the formula (I) have been shown to be effective in causing skin depigmentation. The compounds of the formula (I) have been shown to be effective in causing skin depigmentation and therefore may be useful in the treatment and/or prevention of skin hyperpigmentation.

Yet another use for the compounds of this invention is as trypsin inhibitors. Inhibitors of trypsin have been used clinically in the treatment of certain disorders, such as pancreatitis. The $IC_{50}$ values for the compounds of the invention compare favorably with the pancreatic agents camostat mesilate and nafamostat ($IC_{50}$ s, $1\times10^{-8}$ and $1.3\times10^{-8}$ respectively). The compounds of formula (I) may be used in the same manner as those therapeutic agents.

The compounds of the formula (I) also function as inhibitors of thrombin and factor Xa. Consequently, they may be useful for the treatment of thrombin and/or factor Xa mediated disorders, such as thrombosis.

SUMMARY OF THE INVENTION

The invention relates to novel compounds of the Formula (I):

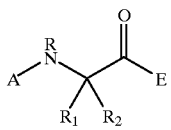

wherein:
A is
selected from the group consisting of substituted $C_{3-8}$ cycloalkylcarbonyl (where the substituents on the $C_{3-8}$ cycloalkyl group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornanecarbonyl (where the substituents on the norbomane group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted norbornenecarbonyl (where the substituents on the norbornene group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted adamantanecarbonyl (where the substituents on the adamantane group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), substituted arylcarbonyl (where the substituents on the aryl group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), heteroarylcarbonyl, substituted heteroarylcarbonyl (where the the substituents on the heteroaryl are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), pyridylcarbonyl, substituted pyridylcarbonyl (where the substituents on the pyridine ring are independently one to three substituents selected from $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), pyrrolocarbonyl, substituted pyrrolocarbonyl (where the substituents on the pyridine ring are independently one to three substituents selected from $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), amido$C_{1-5}$alkylcarbonyl,

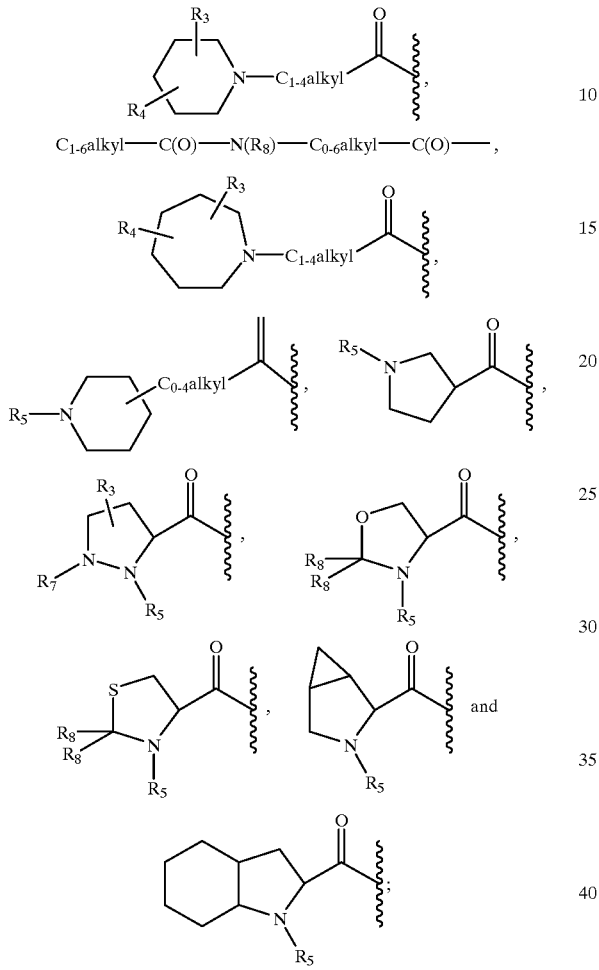

$C_{1-6}$alkyl—C(O)—N($R_8$)—$C_{0-6}$alkyl—C(O)—, a D or L amino acid which is coupled at its carboxy terminus to the nitrogen depicted in formula (I) and is selected from the group consisting of alanine, 2-azetidinecarboxylic acid, glycine, pyrrole-2-carboxylic acid, dehydroproline, proline, substituted proline (where the the substituents on the proline are independently selected from one or more of $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, phenylalkyloxy, phenyl or $C_{1-4}$alkoxycarbonyl), pipecolinic acid, substituted pipecolinic acid (where the the substituents on the piperidine of the pipecolinic acid group are independently selected from one or more of $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, phenylalkyloxy, phenyl or $C_{1-4}$alkoxycarbonyl), valine, norleucine, leucine, tert-leucine, isoleucine, sarcosine, asparagine, serine, methionine, threonine, phenylalanine, 1-naphthalanine, 2-naphthalanine, 2-thienylalanine, 3-thienylalanine, [1,2,3,4]-tetrahydroisoquinoline-1-carboxylic acid and [1,2,3,4]-tetrahydroisoquinoline-2-carboxylic acid, where the amino terminus of said amino acid is connected to a member selected from the group consisting of [1,2,3,4]-tetrahydroisoquinoline-1-carbonyl, [1,2,3,4]-tetrahydroisoquinoline-3-carbonyl, formyl, $C_{1-4}$alkoxycarbonyl, $C_{1-4}$alkylcarbonyl, perfluoro$C_{1-4}$alkylsulfonyl, $C_{1-4}$alkylsulfonyl, amido, N—$C_{1-4}$alkylamido, N,N—$C_{1-4}$dialkylamido, sulfonamido, arylsulfonyl, substituted arylsulfonyl (where the aryl substituents are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), camphorsulfonyl, $C_{1-4}$alkylsulfinyl, arylsulfinyl, substituted arylsulfinyl (where the aryl substituents are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), and arylcarbonyl; or a poly peptide comprised of two amino acids,
where the first amino acid is a D or L amino acid, bound via its carboxy terminus to the nitrogen depicted in formula (I) and is selected from the group consisting of proline and substituted proline (where the the substituents on the proline are independently selected from one or more of $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, aralkyloxy, aryl or $C_{1-4}$alkoxycarbonyl), and the second D or L amino acid, is bound to the amino terminus of said first amino acid, and is selected from the group consisting of aspartic acid, aspartic acid-4-$C_{1-4}$alkyl ester, glutamic acid, glutamic acid-5-$C_{1-4}$alkyl ester, serine, phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine, where the amino terminus of said second amino acid is monosubstituted with a member of the group consisting of $C_{1-6}$alkyl, carboxy$C_{1-8}$alkyl, and $C_{1-10}$alkylcarbonyl;

R, $R_1$ and $R_8$ are each independently
selected from the group consisting of hydrogen and $C_{1-5}$alkyl;

$R_2$ is
selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino $C_{2-5}$alkyl, $C_{1-3}$alkoxy$C_{2-5}$alkyl, phenyl, substituted phenyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl$C_{1-4}$alkyl, substituted pynimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, N-amidinopiperazinyl-N—$C_{0-4}$alkyl, hydroxy $C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl;

$R_3$ and $R_4$ are each independently
  selected from the group consisting of hydrogen, $C_{1-4}$alkyl, perfluoro$C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, $C_{1-4}$alkylcarbonylamino, aryl, substituted aryl (where the substituents on the aryl group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl), $C_{1-4}$alkoxycarbonyl, aminosulfonyl. $C_{1-4}$alkylaminosulfonyl, $C_{1-4}$alkylsulfonylamino and N,N-di-$C_{1-4}$alkylaminosulfonyl;

$R_5$ is
  selected from the group consisting of hydrogen, $C_{1-4}$alkyl and $C_{1-4}$alkylcarbonyl;

$R_7$ is selected from the group consisting of hydrogen, $C_{1-4}$alkyl $C_{1-4}$alkylcarbonyl and aryl (where the substituents on the aryl group are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyl, $C_{1-4}$alkylcarbonylamino or $C_{1-4}$alkoxycarbonyl);

E is
  an unsubstituted or substituted heterocycle selected from the group consisting of imidazolin-2-yl, imidazol-2-yl, oxazolin-2-yl, oxazol-2-yl, thiazolin-2-yl, thiazol-2-yl, thiazol-5-yl, 1,3,4-thiadiazol-2-yl, 1,2,4-thiadiazol-3-yl, 1,2,4-thiadiazol-5-yl, isothiazol-3-yl, 1,2,3-triazol-4-yl, 1,2,3-triazol-5-yl, 1,2,4-triazin-3-yl, 1,3,5-triazin-2-yl, tetrazol-5-yl, isoxazol-3-yl, 1,2,3,4-oxatriazol-5-yl, 1,2,3-oxadiazol-4-yl, 1,3,4-oxadiazol-2-yl, 1,2,4-oxadiazol-3-yl, 1,3,4-oxadiazol-2-yl, 2-pyrazolin-3-yl, pyrazol-3-yl, pyrazin-2-yl, pyridazin-3-yl, pyrimidin-2-yl, 1H-indazole-3-yl, benzoxazol-2-yl, benzimidazol-2-yl, benzothiazol-2-yl, 4,5,6,7-tetrahydro-benzothiazol-2-yl, cinnolin-3-yl, phthalazin-1-yl, naphtho[2,1-d]thiazol-2-yl, naphtho[1,2-d]thiazol-2-yl, quinoxalin-2-yl, 4-oxoquinazolin-2-yl, quinazolin-2-yl, quinazolin-4-yl, purin-2-yl, purin-8-yl, pteridin-2-yl, pteridin-6-yl, oxazolo[4,5-b]pyridin-2-yl, oxazolo[5,4-b]pyridin-2-yl, thiazolo[4,5-b]pyridin-2-yl, thiazolo[5,4-b]pyridin-2-yl and thiazolo[5,4-c]pyridin-2-yl, wherein the substituents on the heterocycle are independently selected from $C_{1-4}$alkyl, perfluoro $C_{1-4}$alkyl, $C_{1-4}$alkoxy, hydroxy, halo, amido, nitro, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkoxycarbonyl, phenyl$C_{1-4}$alkylaminocarbony, aryl, or substituted aryl where the substituents on the aryl are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl;

provided that when
  A is a polypeptide wherein the first amino acid is unsubstituted proline, and the second amino acid is selected from the group consisting of aspartic acid, aspartic acid4-$C_{1-4}$alkyl ester, glutamic acid, glutamic acid-5-$C_{1-4}$alkyl ester, phenylalanine, substituted phenylalanine (where the phenyl substituents are independently selected from one or more of, $C_{1-4}$alkyl, perfluoro $C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine,
  where the amino terminus of said second amino acid is monosubstituted with a member of the group consisting of $C_{1-6}$alkyl, carboxy$C_{1-8}$alkyl, and $C_{1-10}$alkylcarbonyl;

then $R_2$ is selected from the group consisting of substituted phenyl (where the substituents are independently selected from one or more of amidino, hydrazino, amidrazonyl), substituted benzyl (where the substituents on the benzyl are independently selected from one or more of amidino, hydrazino, amidrazonyl), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl $C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), substituted imidazo $C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, and N-amidinopiperazinyl-N—$C_{0-4}$alkyl;

and pharmaceutically acceptable salts and prodrugs thereof.

In one embodiment of the invention is a compound of the formula (I)

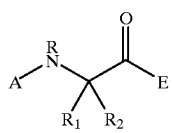

(I)

wherein

A, R, $R_1$, $R_2$, $R_3$, $R_4$, $R_5$, $R_7$, $R_8$ and E are as defined above;

provided that when

A is a poly peptide comprised of two amino acids, then $R_2$ is selected from the group consisting of substituted phenyl (where the substituents are independently selected from one or more of amidino, hydrazino, amidrazonyl), substituted benzyl (where the substituents on the benzyl are independently selected from one or more of amidino, hydrazino, amidrazonyl), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl $C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, and N-amidinopiperazinyl-N—$C_{0-4}$alkyl;

and pharmaceutically acceptable salts and prodrugs thereof.

In a class of the invention is the compound of Formula (I) wherein

A is mono-substituted proline where the substituent is selected from hydroxy, halo or oxo;

R and $R_1$ are both hydrogen;

$R_2$ is guanidino$C_{2-5}$alkyl; and

E is benzothiazol-2-yl;

and pharmaceutically acceptable salts and prodrugs thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating an inflammatory disorder (preferably, an immunomediated inflammatory disorder, most preferably a mast cell mediated inflammatory disorder) in a subject in need thereof comprising administering to the subject a therapeutically effective amount of any of the compounds or pharmaceutical compositions described above.

An illustration of the invention is a method of treating a disorder mediated by trypsin (e.g., pancreatitis) in a subject in need thereof comprising administering to the subject a therapeutically effective amount of any of the compounds or pharmaceutical compositions described above.

Also included in the invention is the use of any of the compounds described above for the preparation of a medicament for treating a condition selected from asthma, allergic rhinitis, rheumatoid arthritis, rheumatoid spondylitis, osteoarthrits, gouty arthritis, arthritic conditions in general (i.e., arthritis), peptic ulcers, ocular and vernal conjunctivitis, inflammatory bowel disease, Crohn's disease, chronic obstructive pulmonary disease (COPD), urticaria, bullous pemphigoid, schieroderma, fibrosis, dermatitis, psoriasis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis in a subject in need thereof.

DETAILED DESCRIPTION OF THE INVENTION

1. Synthetic Methods

The compounds of the invention may be prepared as illustrated according to the procedures and references set forth in detail in the following patents; U.S. Pat. Nos. 5,523,308, 5,164,371, WO 9619491 and WO 9748687. Additional procedures and references are described in the following citations: *Bioorganic & Medicinal Chemistry Letters* 1997, Vol. 7 pp. 1359–1364; *Journal of Medicinal Chemistry* 1996, Vol. 39, pp. 3039–3043; ibid. 1995, Vol. 38, pp. 76–85; ibid. 1994, Vol. 37, pp. 3492–3502. Preferred tryptase inhibitor compounds of the present invention may be prepared according to the detailed examples set forth herein.

Although the claimed compounds are useful as tryptase inhibitors, the preferred compounds of Formula (I) include:

Compound 1
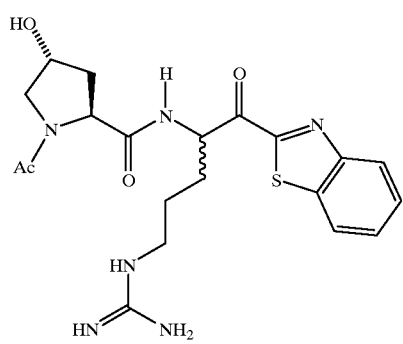
Compound 2
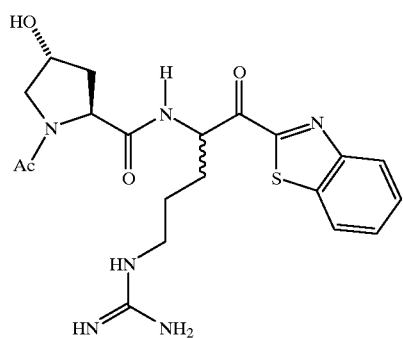
Compound 3
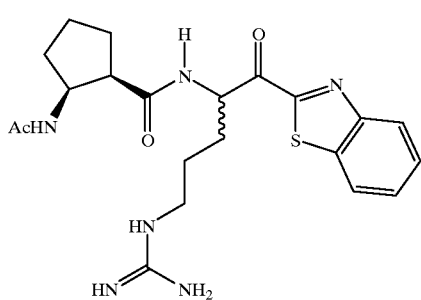
Compound 4
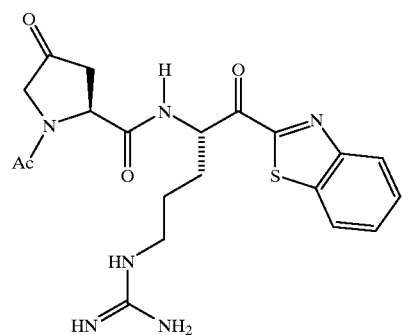
Compound 5
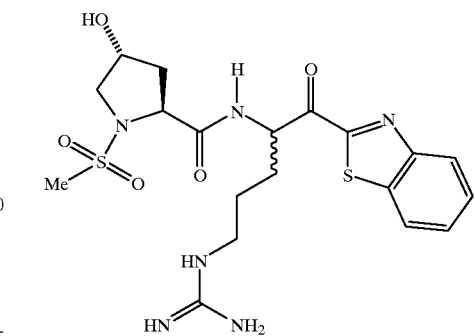
Compound 6
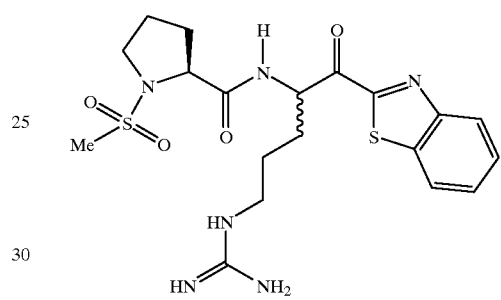
Compound 7
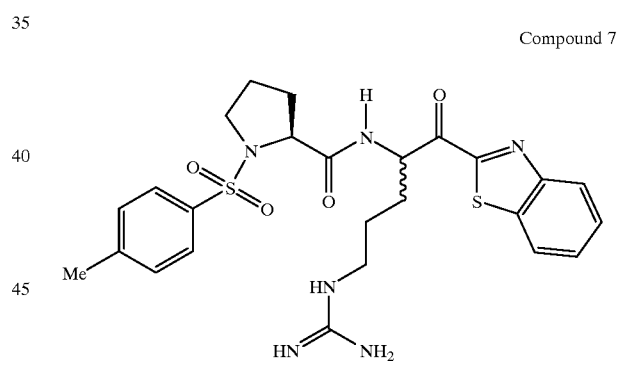
Compound 8
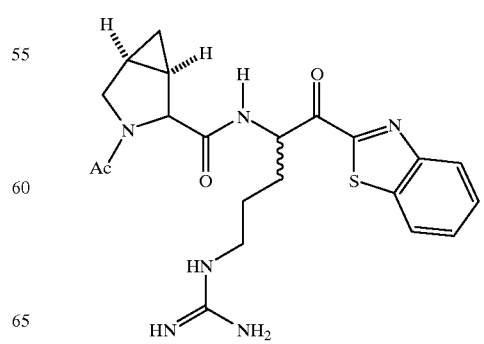

Compound 9
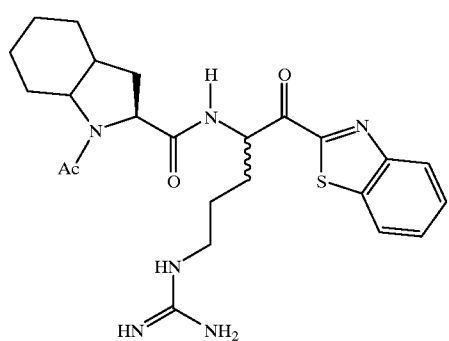
Compound 10
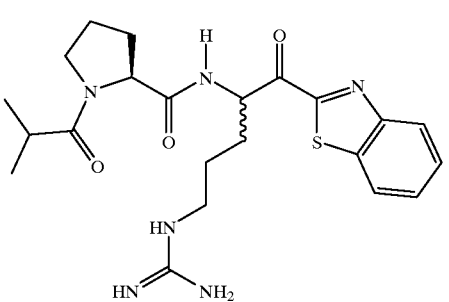
Compound 11
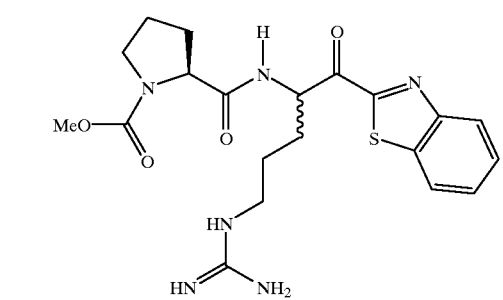
Compound 12
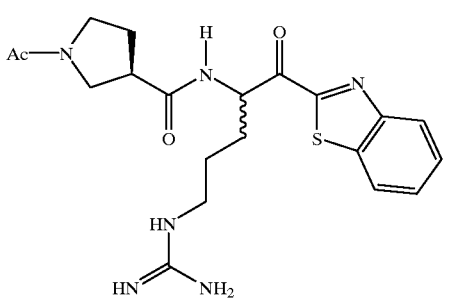
Compound 13
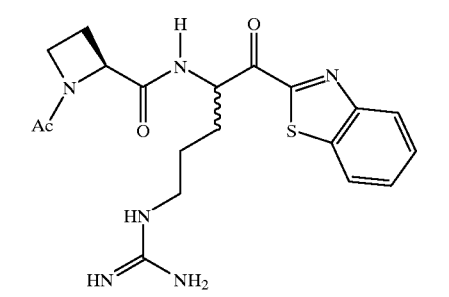
Compound 14
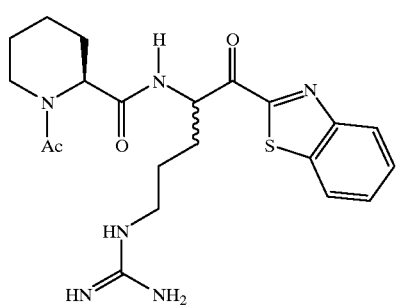
Compound 15
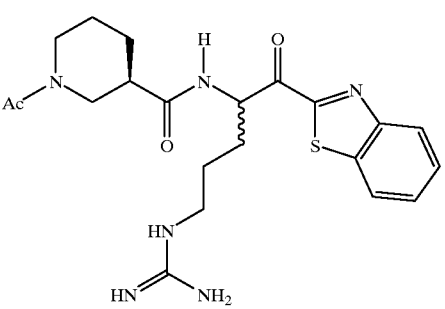
Compound 16
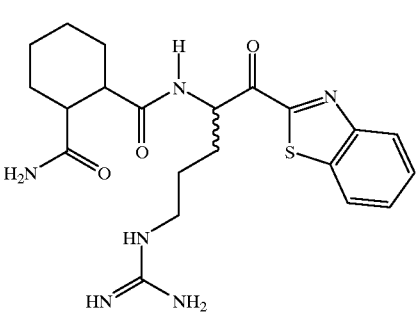
Compound 17
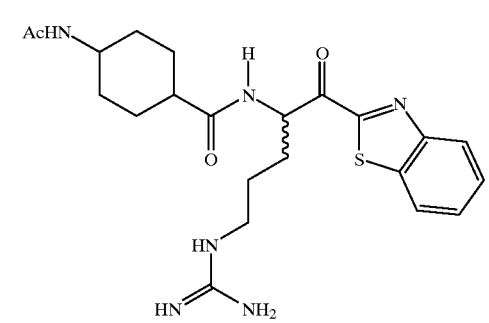
Compound 18
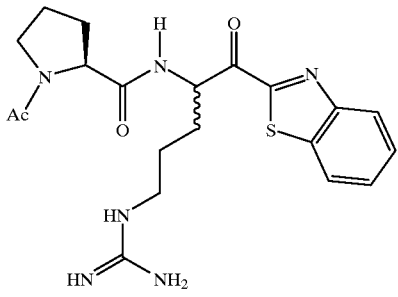

Compound 19
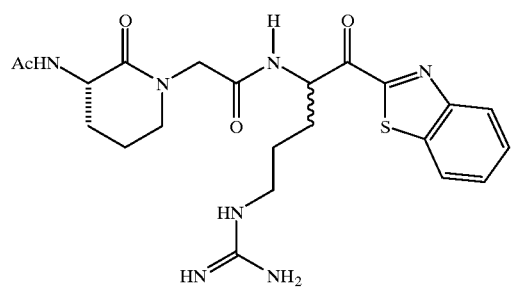
Compound 20
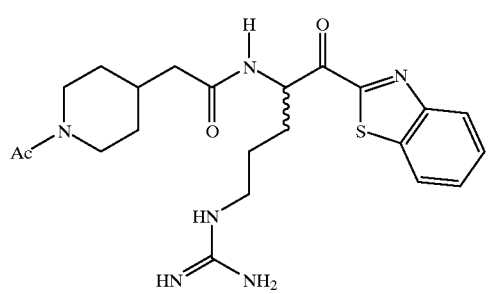
Compound 21
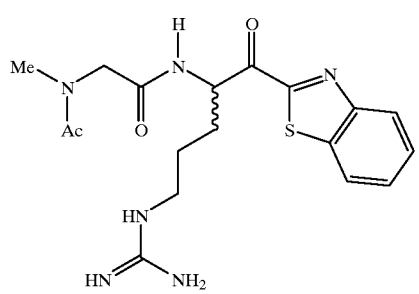
Compound 22
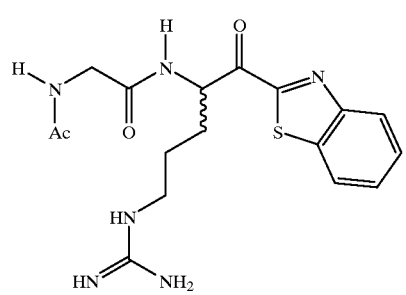
Compound 23
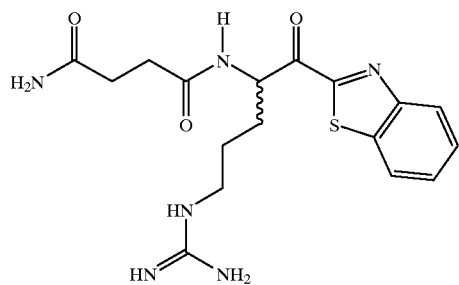
Compound 24
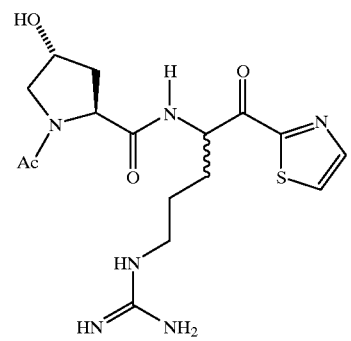
Compound 25
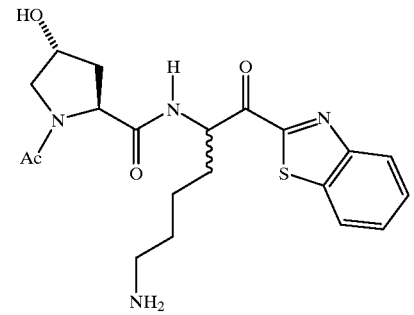
Compound 26
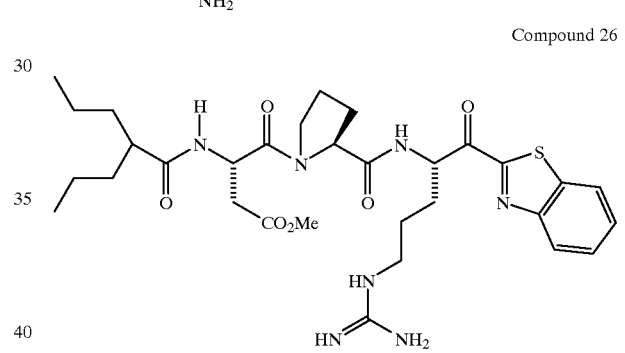
Compound 27
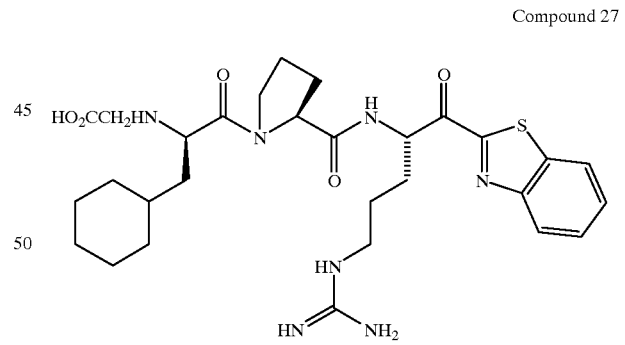
Compound 28
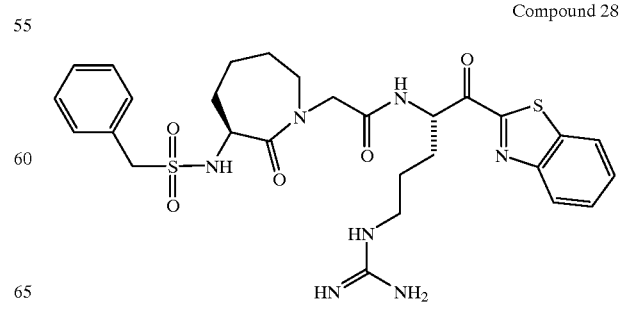

Compound 29
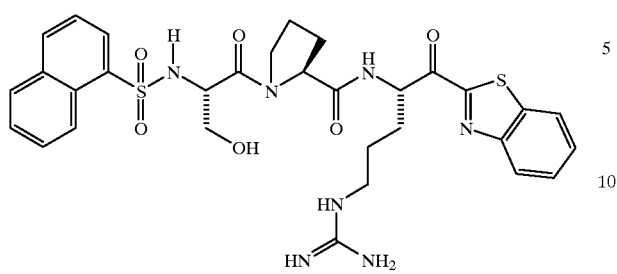
Compound 30
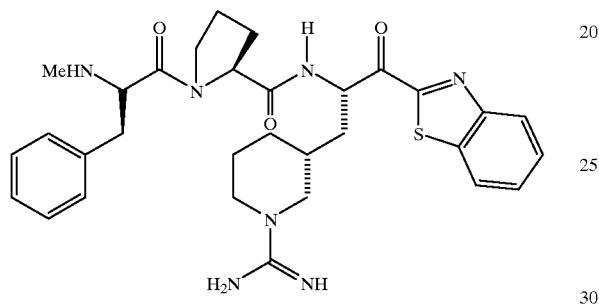
Compound 31
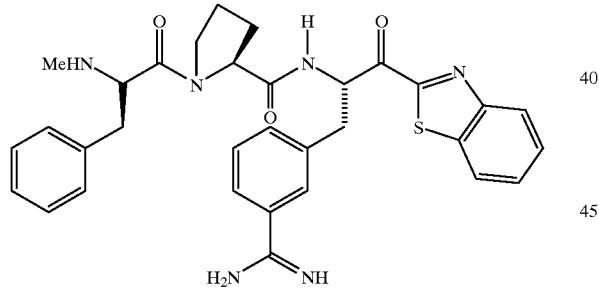
Compound 32
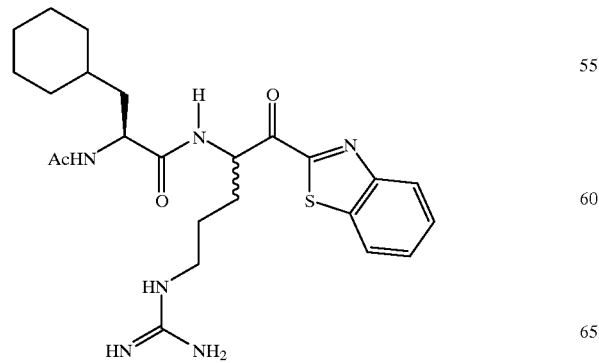
Compound 33
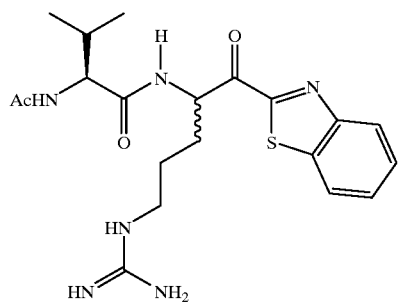
Compound 34
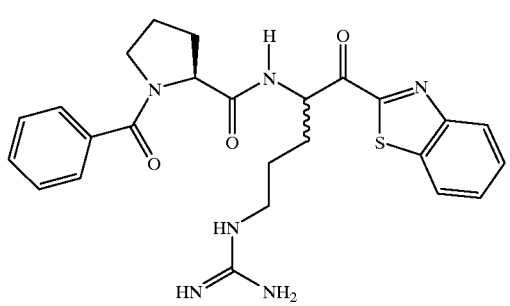
Compound 35
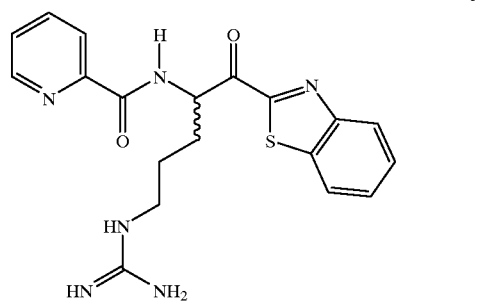
Compound 36
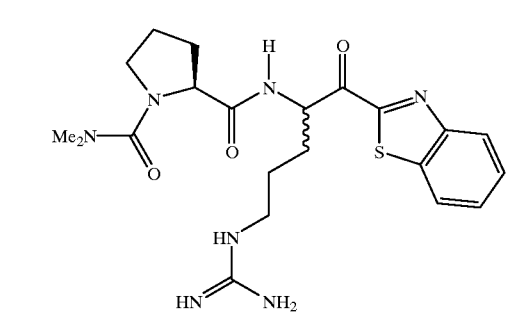
Compound 37
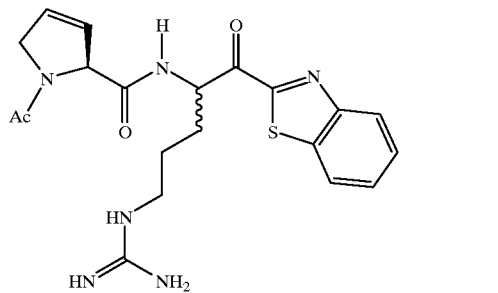

-continued

Compound 38

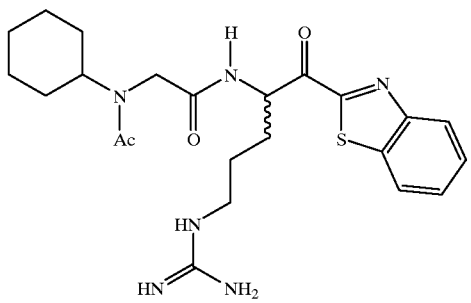

The particularly preferred "A"s are:

C$_{3-8}$ cycloalkylcarbonyl (where the substituents on the C3-8 cycloalkyl group are independently one to two substituents selected from amido, C$_{1-4}$alkylcarbonylamino or C$_{1-4}$alkoxycarbonyl), substituted arylcarbonyl (where the substituents on the aryl group are independently one to two substituents selected from C$_{1-4}$alkyl, perfluoro C$_{1-4}$alkyl, C$_{1-4}$alkoxy, hydroxy, halo, amido), pyridylcarbonyl, substituted pyridylcarbonyl (where the substituents on the pyridine ring are independently one to three substituents selected from C$_{1-4}$alkyl, perfluoro C$_{1-4}$alkyl, C$_{1-4}$alkoxy, hydroxy, halo, amido, N—C$_{1-4}$alkylamido, N,N—C$_{1-4}$dialkylamido, nitro, amino, C$_{1-4}$alkylamino, C$_{1-4}$dialkylamino, carboxy, C$_{1-4}$alkylcabony, C$_{1-4}$alkylcarbonylamino or C$_{1-4}$alkoxycarbonyl), pyrrolocarbonyl, substituted pyrrolocarbonyl (where the substituents on the pyridine ring are independently one to three substituents selected from C$_{1-4}$alkyl, perfluoro C$_{1-4}$alkyl, C$_{1-4}$alkoxy, hydroxy, halo, amido, N—C$_{1-4}$alkylamido, N,N—C$_{1-4}$dialkylamido, nitro, amino, C$_{1-4}$alkylamino, C$_{1-4}$dialkylamino, carboxy, C$_{1-4}$alkylcarbonyl, C$_{1-4}$alkylcarbonylamino or C$_{1-4}$alkoxycarbonyl),

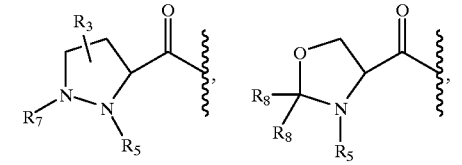

C$_{1-4}$alkyl—C(O)—N(R$_8$)—C$_{1-4}$alkyl—C(O)—,

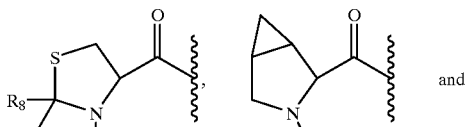

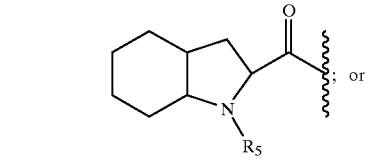

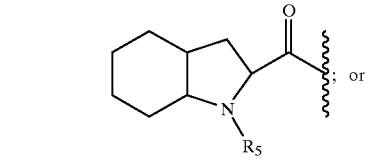

a D or L amino acid which is coupled at its carboxy terminus to the nitrogen depicted in formula (I) and is selected from the group consisting of pyrrole-2-carboxylic acid, dehydroproline, proline, substituted proline (where the the substituents on the proline are independently one to two substituents selected from C$_{1-4}$alkyl, hydroxy, oxo, halo, amido, phenylalkyloxy, or C$_{1-4}$alkoxy), pipecolinic acid, where the amino terminus of said amino acid is connected to a member selected from the group consisting of C$_{1-4}$alkoxycarbonyl, C$_{1-8}$alkylcarbonyl, C$_{1-4}$alkylsulfonyl, amido, N—C$_{1-4}$alkylamido, N,N—C$_{1-4}$dialkylamido, sulfonamido, arylcarbonyl, arylsulfonyl, and substituted arylsulfonyl (where the aryl substituents are independently one to two substituents selected from C$_{1-4}$alkyl, or perfluoro C$_{1-4}$alkyl).

Most preferably, A is substituted proline where the the substituents on the proline are independently one to two substituents selected from C$_{1-4}$alkyl, hydroxy, oxo, halo, amido, phenylalkyloxy, or C$_{1-4}$alkoxy.

The particularly preferred "R$_1$"s are hydrogen and methyl; most preferably, hydrogen.

The particularly preferred "R$_2$"s are selected from the group consisting of aminoC$_{2-5}$alkyl, guanidinoC$_{2-5}$alkyl, amidinoC$_{2-5}$alkyl, C$_{1-5}$alkylaminoC$_{2-5}$alkyl or C$_{1-5}$dialkylamino C$_{2-5}$alkyl.

The particularly preferred "E"s are heterocycles selected from the group consisting of unsubstituted or substituted imidazol-2-yl, oxazolin-2-yl, oxazol-2-yl, thiazol-2-yl, benzoxazol-2-yl, benzimidazol-2-yl, benzothiazol-2-yl, 4,5,6,7-tetrahydro-benzothiazol-2-yl, 4-oxoquinazolin-2-yl, or quinazolin-2-yl, wherein the substituents on the heterocycle are independently one or two substituents selected from C$_{1-4}$alkyl, perfluoro C$_{1-4}$alkyl, C$_{1-4}$alkoxy, hydroxy, halo, amido, N—C$_{1-4}$alkylamido, N,N—C$_{1-4}$dialkylamido, carboxy or C$_{1-4}$alkoxycarbonyl.

2. Biological Methods

The compounds of this invention were tested for their ability to inhibit tryptase and chymase mediated hydrolysis via an in vitro enzyme assay.

Tryptase IC50 Method

The rate of increase in absorbance at 405 nM due to hydrolysis of synthetic chromogenic peptide substrates ([S]:

500 μM N-p-Tosyl-GLY-PRO-LYS-pNA; Sigma T-6140) is measured in the presence and absence of inhibitors (I) with a microplate reader at 37° C. The enzyme reaction is started by the addition of enzyme ([E]: 1.0 nM human Lung Tryptase; Cortex Biochem CP3033). Data is collected over a period of 30 min. and the initial rate of substrate hydrolysis (Vo (mOD/min)) is calculated. Inhibition is calculated by comparing to wells containing no inhibitor (vehicle) and $IC_{50}$s are determined using a four parameter fit logistics model.

Trypsin $IC_{50}$ Method

Inhibition of trypsin-catalyzed hydrolysis rates were measured using the same method as the tryptase procedure. Bovine type 1 trypsin (Sigma) and Spectrozyme® TRY (Cbo-Gly-D-Ala-Arg-pNA.AcOH, American Diagnostics) replaced their tryptase equivalents at concentrations of 3.2 U/ml trypsin and 1.0 mM Spectrozyme® TRY.

TABLE A

| Compound. Number | Tryptase $IC_{50}$ (μM) | N = | Trypsin $IC_{50}$ (μM) | N = |
|---|---|---|---|---|
| 1 | 0.036 ± 0.031 | 8 | 0.021 ± 0.042 | 8 |
| 2 | 0.10 ± 0.02 | 15 | 0.035 ± 0.019 | 11 |
| 3 | 1.7 ± 0.7 | 2 | 0.36 ± 0.03 | 1 |
| 4 | 0.37 ± 0.09 | 5 | 0.037 ± 0.016 | 3 |
| 5 | 0.10 ± 0.01 | 2 | 0.21 | 1 |
| 6 | 0.14 ± 0.08 | 2 | 0.11 | 1 |
| 7 | 1.4 ± 0.8 | 3 | 0.23 ± 0.11 | 3 |
| 8 | 0.11 ± 0.04 | 3 | 0.19 | 1 |
| 9 | 0.69 ± 0.30 | 2 | 0.067 ± 0.051 | 2 |
| 10 | 0.18 ± 0.01 | 2 | 0.019 | 1 |
| 11 | 2.4 ± 0.9 | 2 | 0.039 | 1 |
| 12 | 14 | 1 | 8.8 | 1 |
| 13 | 0.32 ± 0.08 | 8 | 0.053 ± 0.062 | 4 |
| 14 | 0.27 ± 0.08 | 3 | 0.048 ± 0.020 | 2 |
| 15 | 12 ± 2.0 | 2 | 0.6 | 1 |
| 16 | 0.18 ± 0.07 | 2 | 0.16 | 1 |
| 17 | 9.4 ± 5.7 | 2 | 2.4 | 1 |
| 18 | 0.15 ± 0.04 | 6 | 0.029 ± 0.017 | 6 |
| 19 | 12 ± 5.0 | 2 | 0.32 | 1 |
| 20 | 20 ± 12 | 2 | 1.0 | 1 |
| 21 | 2.4 ± 0.6 | 2 | 0.17 ± 0.06 | 2 |
| 22 | 1.6 ± 0.7 | 2 | 0.25 ± 0.12 | 2 |
| 23 | 0.26 ± 0.01 | 3 | 0.093 ± 0.068 | 2 |
| 24 | 0.39 ± 0.14 | 6 | 0.27 ± 0.13 | 4 |
| 25 | 0.35 ± 0.08 | 5 | 0.18 ± 0.10 | 3 |
| 26 | 0.11 ± 0.01 | 2 | 0.048 ± 0.001 | 2 |
| 27 | 0.034 ± 0.003 | 2 | 0.036 ± 0.001 | 3 |
| 28 | 0.10 ± 0.04 | 2 | 0.042 ± 0.001 | 3 |
| 29 | 0.014 ± 0.005 | 2 | 0.058 ± 0.012 | 5 |
| 30 | 0.036 ± 0.004 | 2 | 0.11 ± 0.07 | 5 |
| 31 | 0.29 ± 0.03 | 2 | 0.24 | 1 |
| 32 | 0.44 | 1 | 0.017 | 1 |
| 33 | 0.18 ± 0.01 | 2 | 0.019 | 1 |
| 34 | 0.34 | 1 | 0.046 | 1 |

In addition, one of ordinary skill in the art can readily determine the utility of the compounds of formula (I) to act as tryptase inhibitors for treating asthma by using an in vivo sheep model which is described in Abraham et al. *Amer. J. of Respir. and Crit. Care Med.* 1996, 154, 649–654; and Clark et al. *Amer. J. of Respir. and Crit. Care Med.* 1995, 152, 2076–2083.

The terms used in describing the invention are commonly used and known to those skilled in the art. However, the terms that could have other meanings are defined. "CBZ" refers to benzyloxycarbonyl. "BOC" refers to t-butoxycarbonyl and "Ts" refers to toluenesulfonyl. "DCC" refers to 1,3-dicyclohexylcarbodiimide, "DMAP" refers to 4-N'N-dimethylaminopyridine and "HOBT" refers to 1-hydroxybenzotriazole hydrate. "Dansyl" refers to 5-dimethylamino-1-naphthalenesulfonamide and "Fmoc" refers to N-(9-fluorenylmethoxycarbonyl). CAS#" refers to Chemical Abstracts Service Registry Number. MS (ES) refers to positive ion electrospray mass spectroscopy and m/z refers to mass to charge ratio.

Typically the compounds of Formula I are isolated and used directly or as their pharmaceutically acceptable salts and prodrugs. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexanesulfamic and saccharic. Examples of such prodrugs include, but are not limited to, carbamates, N-acylamidines, N-acylguanidines, ketals, and enolethers.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

As used herein, unless otherwise noted alkyl and alkoxy whether used alone or as part of a substituent group, include straight and branched chains having 1 to 8 carbon atoms, or any number within this range. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl and 2-methylpentyl. Alkoxy radicals are oxygen ethers formed from the previously described straight or branched chain alkyl groups. Cycloalkyl groups contain 3 to 8 ring carbons and preferably 5 to 7 ring carbons. Similarly, alkenyl and alkynyl groups include straight and branched chain alkenes and alkynes having 1 to 8 carbon atoms, or any number within this range.

The term "aryl" as used herein refers to an aromatic group such as phenyl and naphthyl.

The term "heteroaryl" as used herein represents a stable unsubstituted or substituted five or six membered monocyclic aromatic ring system or a nine or ten membered benzo-fused heteroaromatic ring system which consists of carbon atoms and from one to six heteroatoms (preferably, one to four heteroatoms) selected from N, O or S. The heteroaryl group may be attached at any heteroatom or carbon atom which results in the creation of a stable structure. Examples of heteroaryl groups include, but are not limited to pyridinyl, pyrazinyl, pyridazinyl, pyrimidinyl, thiophenyl, furanyl, imidazolyl, isoxazolyl, oxazolyl, pyrazolyl, pyrrolyl, thiazolyl, thiadiazolyl, triazolyl, tetrazolyl, purinyl, benzimidazolyl, benzofuranyl, benzothienyl, benzisoxazolyl, benzoxazolyl, benzopyrazolyl, indolyl, benzothiazolyl, benzothiadiazolyl, benzotriazolyl or quinolinyl.

When a particular group (e.g., aryl, heteroaryl) is substituted, that group may have one or more substituents (preferably, one to five, more preferably, one to three, most preferably, one or two substituents) independently selected from the listed substituents.

The term "aralkyl" (e.g., $arC_{1-4}$alkyl) means an alkyl group substituted with an aryl group (e.g., benzyl, phenylethyl). Similarly, the term "aralkoxy" indicates an alkoxy group substituted with an aryl group (e.g., benzyloxy). The term "aminoalkyl" refers to an alkyl group substituted with an amino group (ie., -alkyl-$NH_2$). The term "alkylamino" refers to an amino group substituted with an alkyl group (i.e., —NH-alkyl). The term "dialkylamino" refers to an amino group which is disubstituted with alkyl groups wherein the alkyl groups can be the same or different (.e., —N-[alkyl]$_2$).

The term "amido" refers to —C(O)—NH$_2$. N-Alkylamido and N,N-dialkylamido refer to —C(O)—NH-alkyl and —C(O)—N(alkyl)$_2$, respectively. Similarly, sulfoxamido refers to —SO$_2$—NH$_2$.

The term "amidrazonyl" as used herein refers to —C(=NH)NH—NH$_2$ or —C(NH$_2$)=N—NH$_2$, preferably, —C(=NH)NH—NH$_2$.

The term "acyl" as used herein means an organic radical having 2 to 6 carbon atoms (branched or straight chain) derived from an organic acid by removal of the hydroxyl group.

The term "halo" refers to a halogen and shall include iodine, bromine, chlorine and fluorine.

The term "oxo" refers to =O.

Whenever the term "alkyl" or "aryl" or either of their prefix roots appear in a name of a substituent (e.g., aralkyl, dialkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The compounds of formula (I) are useful for treating inflammatory disorders (preferably, immunomediated inflammatory disorders, most preferably, mast cell mediated inflammatory disorders). Examples of immunomediated inflammatory disorders for which the compounds of the present invention are useful include, but are not limited to, asthma, allergic rhinitis, rheumatoid arthritis, rheumatoid spondylitis, osteoarthritis, gouty arthritis, arthritic conditions in general (i.e., arthritis), peptic ulcers, ocular and vernal conjunctivitis, inflammatory bowel disease, chronic obstructive pulmonary disease ("COPD"; see Grashoff, W. F. et al., American Journal of Pathology, 151(6):1785–90, December 1997), Crohn's disease, urticaria, bullous pemphigoid, scleroderma, fibrosis, dermatitis, psoriasis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis.

The compounds of the formula (I) have also been shown to be effective in causing skin depigmentation and therefore may be useful in the treatment and/or prevention of skin hyperpigmentation.

The compounds of the formula (I) also function as inhibitors of thrombin and factor Xa. Consequently, they may be useful for the treatment of thrombin and/or factor Xa mediated disorders, such as thrombosis.

The compounds can be administered by any conventional route including but not limited to; oral, intravenous, intraperitoneal, intramuscular, subcutaneous, intranasal, topical, inhalation, suppository, and dermal patch, where the preferred route is inhalation. Doses can range from about 0.001 to about 2000 mg/kg/day (preferably, about 0.001 to about 200 mg/kg/day) of inhibitor admixed with a suitable pharmaceutical carrier. Doses can be given in a bolus fashion or over a time period at about 0.001–2000 mg/kg/day ranging from several minutes to several days.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, via inhalation or via transdermal skin patches well known to those of ordinary skill in that art. To be administered in the form of a transdermal delivery system, the dosage administration will, of course, be continuous rather than intermittent throughout the dosage regimen.

Optimal dosages of the compounds of formula (I) to be administered for the treatment of or prevention of immunomediated inflammatory disorders may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Therapeutic agents that may be useful for administration in combination with compounds of formula (I) include β-adrenergic agonists (e.g. albuterol, terbutaline, formoterol, fenoterol, prenaline and the like) methylxanthines (e.g. caffeine, theophylline, aminophylline, theobromine, and the like) and corticosteroids (e.g. beclomethasome, triamcinolone, flurisolide, dexamethasone, hydrocortisone, prednisone and the like). In general, one of ordinary skill in the art, acting in reliance upon personal knowledge and the disclosure of this application, will be able to ascertain the amounts of these respective therapeutic agents and the amount of the compound of the formula (I) which should be administered to a subject to treat a given immunomediated inflammatory disease. A "therapeutically effective amount," when referring to a combination of two or more agents, means an amount of each of the combined agents which is effective in eliciting the desired biological or medical response. For example, the therapeutically effective amount of a composition comprising Compound 1 and albuterol would be the amount of Compound 1 and the amount of albuterol that, when taken together, have a combined effect which is therapeutically effective. In accordance with the methods of treatment of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

Additionally, the method of treating immunomediated inflammatory disorders of the present invention may also be carried out using a pharmaceutical composition comprising any of the compounds of formula (I) and a pharmaceutically acceptable carrier. The compositions for treating inflammatory cell mediated inflammatory disorders include oral, inhalant, intranasal, intravenous, suppository, sustained release formulations, and topical preparations as well as devices used to administer such preparations. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Compositions useful for topical administration include liquid forms, emulsions, suspensions, gels, creams, ointments and sprays. Compositions suitable for inhalation include aerosolized solutions, emulsions, suspensions and dry powders. Compositions useful for parenteral administration include sterile solutions, emulsions and suspensions.

The pharmaceutical compositions can be prepared using conventional pharmaceutical excipients and compounding techniques. To prepare the pharmaceutical compositions of this invention, one or more compounds of formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. Oral dosage forms may be elixers, syrups, capsules, caplets, pills, tablets and the like. Where the typical solid carrier is an inert substance such as lactose, starch, glucose, methyl cellulose, magnesium sterate, dicalcium phosphate, mannitol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

EXAMPLE 1

(2S,4R)-1-Acetyl-N-[(1S)-4-[(aminoiminomethyl) amino]-1-(2-benzothiazolylcarbonyl)butyl]-4-hydroxy-2-pyrrolidinecarboxamide STEP a

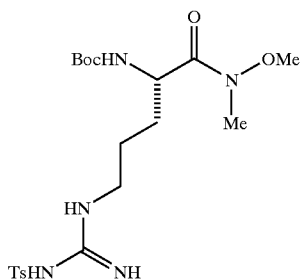

1a

Benzotriazol-1-yloxy-tris(dimethylamino)phosphonium hexafluorophosphate (BOP reagent; 113.5 g, 0.256 mol) was added in one portion to a stirred solution of N-α-t-Boc-N$^G$-(p-toluenesulfonyl)-L-arginine (Boc-Arg(Ts)-OH; 100 g, 0.233 mol), N,O-dimethylhydroxylamine hydrochloride (34.2 g, 0.350 mol), triethylamine (97 mL, 0.696 mol) in dry N,N-dimethylformamide (2.5 L) under argon at 5° C. The reaction mixture was allowed to slowly warm to room temperature over 1 h, filtered through diatomaceous earth and concentrated in vacuo at 60° C. The residue was dissolved in CH$_2$Cl$_2$ (1 L), washed sequentially with H$_2$O, saturated aqueous NaHCO$_3$ (2×), 1N HCl (2×), brine, dried (Na$_2$SO$_4$) and concentrated in vacuo to give a thick syrup. The syrup was recrystallized from ethyl acetate (300 mL) at room temperature over 16 h. The resulting white solid was isolated by filtration, rinsed with cold ethyl acetate followed by diethylether, and dried in vacuo to afford 1a (DiMaio et al. *Journal of Medicinal Chemistry* 1992, 357 3331).

STEP b

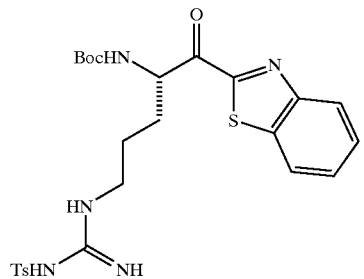

1b 2.5 M n-Butyllithium in hexanes (135 mL, 338 mmol) was added dropwise to a stirred solution of benzothiazole (56.8 g, 420 mmol) in dry tetrahydrofuran (600 mL) at 78° C. under argon at a rate that kept the reaction temperature below −64° C. Upon completion of addition, the reaction mixture was stirred for 30 min at −70° C. and a solution of 1a (20.0 g, 42.4 mmol) in dry tetrahydrofuran (500 mL) was added at a rate that maintained the reaction temperature below −70° C. The resulting mixture was allowed to slowly warm to room temperature over 2 h and then quenched with saturated aqueous NH$_4$Cl (250 mL). The resulting organic layer was separated, washed with brine, dried (Na$_2$SO$_4$) and concentrated in vacuo. The residue was triturated 3 times with hexane and purified by chromatography on silica gel eluting with ethyl acetate/hexane (3:2) to furnish 1b as an amber solid.

STEP c

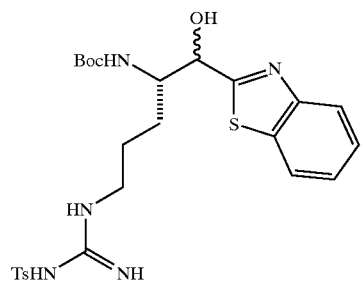

1c

NaBH$_4$ (3.7 g, 0.097 mol) was added portion-wise to a stirred solution of 1b (17.8 g, 0.033 mmol) in dry methanol (165 mL) under argon at −30° C. After 3 h, the reaction was quenched with acetone (30 mL) and concentrated in vacuo. The residue was dissolved in CH$_2$Cl$_2$, washed sequentially with 10% aqueous citric acid, water, brine, dried (Na$_2$SO$_4$) and concentrated in vacuo to give 1c as a yellow solid.

STEP d

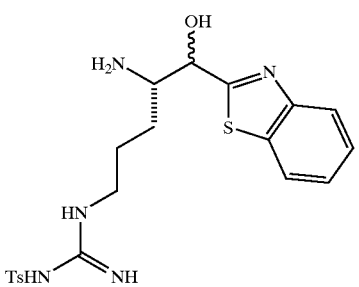

1d

STEP f

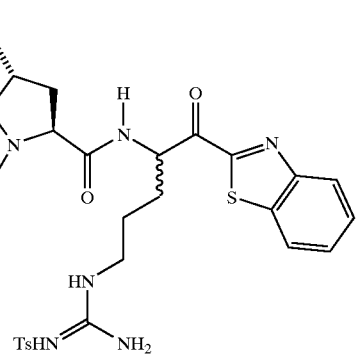

1f

Intermediate 1c (1.0 g, 1.8 mmol) was treated with a solution of trifluoroacetic acid/$CH_2Cl_2$ (1:1 v/v; 50 mL) and stirred at room temperature for 2 h. The reaction mixture was concentrated in vacuo, dissolved in ethyl acetate, and extracted with a 1:1 mixture (v/v) of brine and 10% aqueous $Na_2CO_3$. The organic layer was extracted once with brine, dried ($Na_2SO_4$), and concentrated in vacuo to furnish 1d as a yellow solid.

The Dess-Martin periodinane (18.7 g, 0.044 mol) was added to a solution of 1d (14.9 g, 0.022 mol) in $CH_2Cl_2$ (220 mL) under argon at room temperature and stirred for 1 h. The reaction mixture was quenched with a solution containing 20% $Na_2S_2O_3$ (w/w) in saturated aqueous $NaHCO_3$ and the mixture was stirred at room temperature for 2 h. The organic layer was separated, washed with brine, dried ($Na_2SO_4$) and concentrated in vacuo to give 1e as a white solid.

STEP e

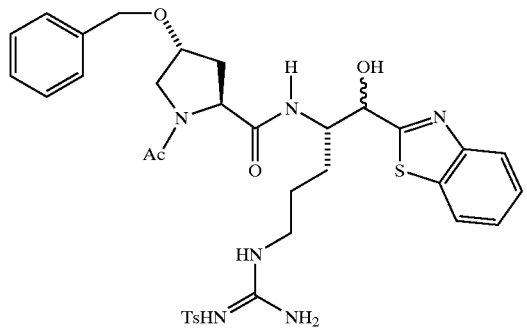

1e

STEP g

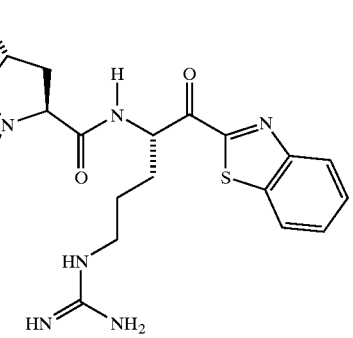

Compound 1

Intermediate 1d (12.12 g, 0.027 mol), trans-1-acetyl4-benzyloxy-L-proline (7.13 g, 0.027 mol; *Bioorganic and Medicinal Chemistry Letters* 1996, Vol. 6, pp. 2225–2230) and 1-hydroxybenzotriazole hydrate (HOBT; 9.16 g, 0.068 mol) were combined and dissolved in N,N-dimethylformamide (270 mL). To this solution was added 1,3-dicyclohexylcarbodiimide (DCC; 13.99 g, 0.068 mol) and the reaction was stirred under argon at room temperature for 18 h. The reaction mixture was filtered and the filtrate was diluted with water (ca 800 mL), extracted with ethyl acetate (3×), washed with water, dried ($Na_2SO_4$) and concentrated in vacuo. The residue was purified by chromatography on silica gel eluting with $CH_2Cl_2$/methanol (19:1) to afford 1d as a white solid.

Intermediate 1e was dissolved in anhydrous anisole (ca. 12 mL) in a teflon reaction vessel, placed on a HF apparatus, and cooled to −78° C. Anhydrous HF (ca. 38 mL) was condensed into the reaction vessel and the reaction was warmed to 0° C. The reaction was stirred at 0° C. for 6 h, concentrated in vacuo and triturated with diethyl ether (3×) to give a white solid. This solid was purified by reverse-phase HPLC eluting with a gradient of water/acetonitrile/trifluoroacetic acid (90:10:0.2 to 70:30:0.2) on Bondapak C-18 column (40×300 mm; 15–20μ) at 40 mL/min over 60 min. The fractions containing the later eluting diastereomer were combined and lyophilized to give 1 as the trifluoroacetate salt; MS (ES) m/z 447 ($MH^+$).

EXAMPLE 2

(2S,4R)-1-Acetyl-N-[4-[(aminoiminomethyl)amino]-1-(2-benzothiazolylcarbonyl)butyl]-4-hydroxy-2-pyrrolidinecarboxamide

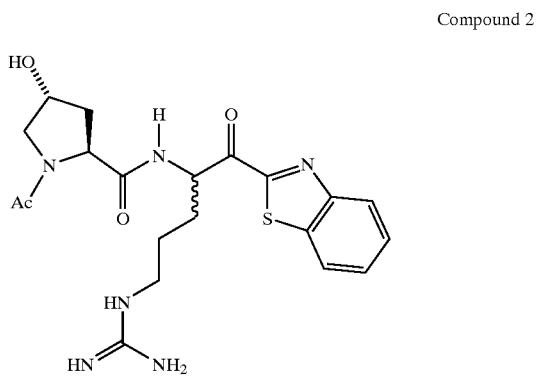

Compound 2

Compound 2 was prepared in the same way as described in Example 1 with the exception that both L- and D-arginine epimers were collected during the reverse-phase HPLC purification to afford a 1.1:1 mixture of epimers. The trifluoroacetate salt of 2 was converted to the HCl salt by dissolving it into 0.1 N aqueous HCl and concentrating in vacuo 3 times. The resulting glass was dissolved in water and lyophilized to afford the HCl salt of 2 as a light yellow solid; MS (ES) m/z 447 (MH$^+$).

EXAMPLE 3 cis-2-Acetylamino-N-[(1S)-4-[(aminoiminomethyl)amino]-1-(2-benzothiazolylcarbonyl)butyl]-1-cyclopentanecarboxamide STEP a

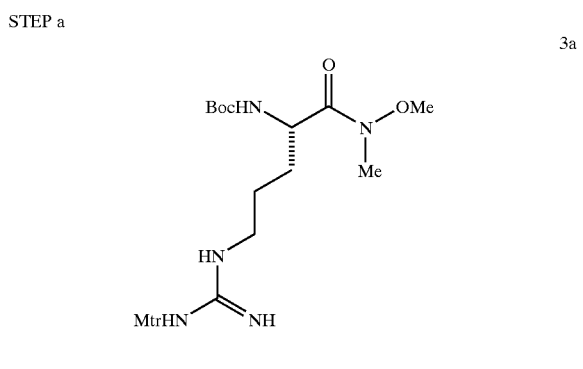

3a

Benzotriazol-1-yloxy-tris(dimethylamino)phosphonium hexafluorophosphate (BOP reagent; 25.0 g, 56 mmol) was added in one portion to a stirring solution of N-α-t-Boc-N$^G$-(4-methoxy-2,3,6-trimethylbenzenesulfonyl)-L-arginine (Boc-Arg(Mtr)-OH; 24.96 g, 51.3 mmol), N,O-dimethylhydroxylamine hydrochloride (7.6 g, 56 mmol), triethylamine (22 mL, 154 mmol) in dry N,N-dimethylformamide (100 mL) under argon at 0° C. The reaction mixture was allowed to slowly warm to room temperature over 2 h, filtered through diatomaceous earth, and concentrated in vacuo. The residue was dissolved in ethyl acetate, washed with H$_2$O (3×), IM aqueous KHSO$_4$, saturated aqueous NaHCO$_3$, brine, dried (Na$_2$SO$_4$) and concentrated in vacuo. The residue was purified by chromatography on silica gel eluted with ethyl acetate/CH$_2$Cl$_2$ (3:1) to give 3a as a white solid (see WO 9630396, Example 2).

STEP b

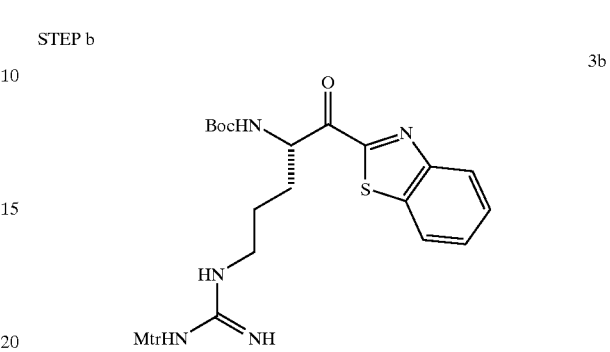

3b 2.5 M n-Butyllithium in hexanes (164 mL, 410 mmol) was added dropwise at −78° C. under argon to a stirring solution of benzothiazole (69.2 g, 512 mmol) in dry tetrahydrofuran (1000 mL) at a rate that kept the reaction temperature below −64° C. Upon completion of addition, the reaction mixture was stirred for 30 min at −70° C. and a solution of 3a (27.11 g, 51.2 mmol) in dry tetrahydrofuran (200 mL) was added at a rate that maintained the reaction temperature below −70° C. The reaction was stirred for 15 min, quenched with saturated aqueous NH$_4$Cl (500 mL), and stirred for 16 h at room temperature. The resulting organic layer was separated, diluted with ethyl acetate, washed with water, brine, dried (Na$_2$SO$_4$) and concentrated in vacuo. The thick syrupy residue was triturated with hexanes (3×) and purified by chromatography on silica gel eluting with CH$_2$Cl$_2$/ethyl acetate (7:3) to afford 3b as a light-yellow solid.

STEP c

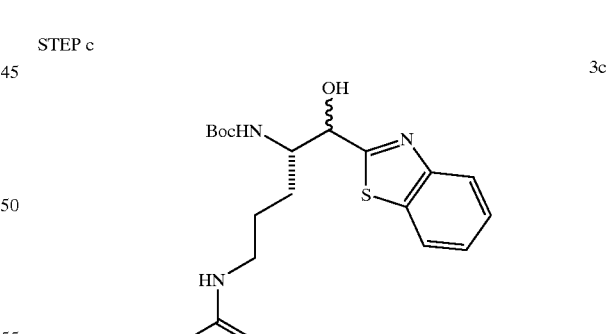

3c

NaBH$_4$ (4.9 g, 129 mmol) was added portion-wise to a stirring solution of 3b (15.0 g, 27.4 mmol) in dry methanol (200 mL) under argon at 0° C. The reaction mixture was slowly warmed to room temperature over 1 h, quenched with acetone (30 mL), and concentrated in vacuo. The residue was dissolved in ethyl acetate, washed with water (2×), brine, dried (Na$_2$SO$_4$) and concentrated in vacuo to give 3c as a yellow solid.

STEP d

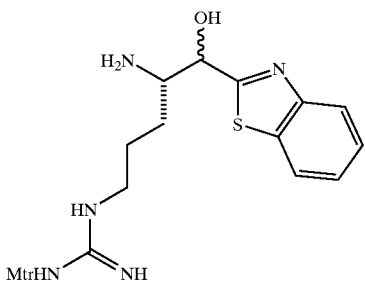

3d p-Toluenesulfonic acid monohydrate (TsOH.H$_2$O) was added at room temperature to solution of 3c (1.0 g, 1.8 mmol) in CH$_2$Cl$_2$ until the solution was saturated. The reaction was stirred at room temperature for 6 h, diluted with ethyl acetate, extracted twice with a 1:1 mixture (v/v) of brine and 10% aqueous Na$_2$CO$_3$, dried (Na$_2$SO$_4$), and concentrated in vacuo to give 3d as a yellow solid.

STEP e

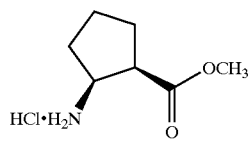

3e

To a slurry of (±)-cis-2-amino-1-cyclohexanecarboxylic acid (2.11 g, 12.1 mmol) in dry methanol (25 mL) and 2,2-dimethoxypropane (6.1 mL, 49.6 mmol) was added 4 M HCl in 1,4-dioxane (6.1 mL, 24.2 mmol) at 5° C. while stirring under argon. After the addition, the resulting solution was warmed to room temperature, stirred for 18 h, concentrated in vacuo, and triturated with diethyl ether to afford 3e as a white solid.

STEP f

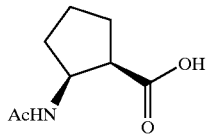

3f

Compound 3e (850 mg, 4.7 mmol) was dissolved in CH$_2$Cl$_2$ (50 mL), cooled to 5° C., and treated with triethylamine (1.4 mL, 10 mmol). Acetyl chloride (370 μL, 5.2 mmol) in CH$_2$Cl$_2$ (10 mL) was added dropwise over 5 min at 5° C. After 2 hours, the reaction mixture was concentrated in vacuo and the residue was partially dissolved in ethyl acetate and filtered through diatomaceous earth. The filtrate was concentrated in vacuo an the residue was dissolved in tetrahydrofuran (25 mL) and diluted with a solution of LiOH (294 mg, 7 mmol) in H$_2$O (25 mL). The reaction mixture was stirred at room temperature for 3 hours, acidified to pH 2–3 with 1 N aqueous HCl, diluted with brine (50 mL), and the layers were separated. The aqueous layer was extracted with tetrahydrofuran (2×) and the combined organic extracts were dried over Na$_2$SO$_4$, filtered, and concentrated in vacuo to furnish 3f as a white solid.

STEP g

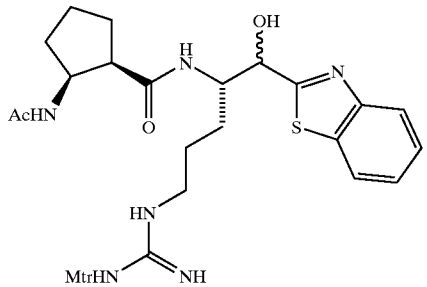

3g

A solution of 3d (910 mg, 1.8 mmol), 3f (308 mg, 1.8 mmol), and 1-hydroxybenzotriazole hydrate (HOBt.H$_2$O; 243 mg, 1.8 mmol) in acetonitrile (50 mL) was treated with 1,3-dicyclohexylcarbodiimide (DCC; 825 mg, 4 mmol) at room temperature while stirring under argon. After 16 h, the reaction was quenched with water (50 mL), stirred for 1 hour, filtered through diatomaceous earth and concentrated in vacuo. The residue was extracted twice with ethyl acetate (50 mL) and the combined organic layers were extracted sequentially with 1M aqueous KHSO$_4$, saturated aqueous NaHCO$_3$ brine, dried (Na$_2$SO$_4$), and concentrated in vacuo. The residue was purified by chromatography on silica gel eluting with a step gradient starting at CH$_2$Cl$_2$/MeOH (39:1) to CH$_2$Cl$_2$/MeOH (19:1) to give 3 g as a white foam.

STEP h

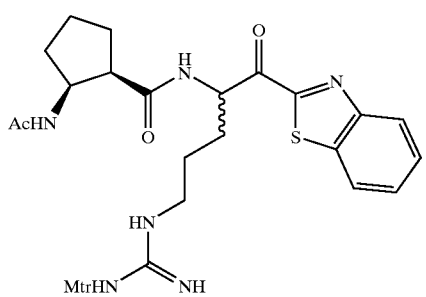

3h

Dess-Martin periodinane (630 mg, 1.43 mmol) was added to a solution of 3 g (630 mg, 0.96 mmol) in CH$_2$Cl$_2$ (20 mL) under argon at room temperature and stirred for 60 min. The reaction mixture was quenched with a solution containing 20% Na$_2$S$_2$O$_3$ (w/w) in saturated aqueous NaHCO$_3$ and the mixture was stirred at room temperature for 2 h. The organic layer was separated, washed with brine, dried (Na$_2$SO$_4$), concentrated in vacuo. The residue was purified by chromatography on silica gel eluting with CH$_2$Cl$_2$/MeOH (39:1) to give 3h as a white solid.

STEP i

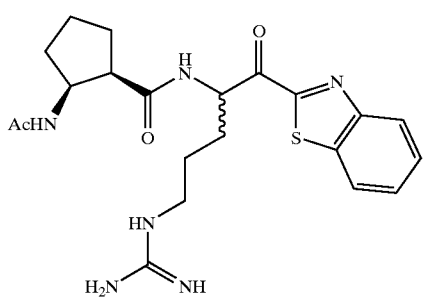

Compound 3

A solution of 3 h (480 mg, 0.73 mmol) in trifluoroacetic acid (10 mL) for 6 h at room temperature. The reaction mixture was concentrated in vacuo and triturated with diethyl ether (3×) to give a white solid. This solid was purified by reverse-phase HPLC eluting with a gradient of water/acetonitrile/trifluoroacetic acid (90:10:0.2 to 70:30:0.2) on Bondapak C-18 column (40×300 mm; 15–20μ) at 40 mL/min over 60 min. The fractions containing both arginine epimers were combined and lyophilized to give 3 as the trifluoroacetate salt; MS (ES) m/z 445 (MH$^+$).

EXAMPLE 4

(2S)-1-Acetyl-N-[4-[(aminoiminomethyl)amino]-1-(2-benzothiazolylcarbonyl)butyl]-4-oxo-2-pyrrolidinecarboxamide STEP a

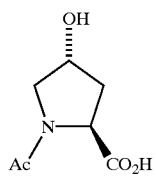

4a

Acetyl chloride (3.3 mL, 46 mmol) was added dropwise to a solution of trans-4-benzyloxy-L-proline hydrochloride (H-Hyp(OBzl)-OMe.HCl; 12.5 g, 46 mmol), triethylamine (6.4 mL, 46 mmol) in pyridine (150 mL) at 0° C. while stirring under argon. The reaction mixture was stirred for 30 min at 0° C. then slowly warmed to room temperature over 16 h. The reaction mixture was concentrated in vacuo, diluted with CH$_2$Cl$_2$, washed with 1 N aqueous HCl (3×), 10% aqueous Na$_2$CO$_3$, saturated aqueous NaHCO$_3$, brine, dried (MgSO$_4$) and concentrated in vacuo. The residue was purified by chromatography on silica gel eluting with ethyl acetate/hexane (3:2) to give Ac-Hyp(OBzl)-OMe as an oil.

The oil was dissolved in tetrahydrofuran (458 mL), cooled to 0° C., and treated dropwise with 0.2 M aqueous LiOH (458 mL, 92 mmol) and stirred 30 min. The reaction mixture was concentrated in vacuo, acidified with 1N aqueous HCl, and extracted with ethyl acetate (3×). The combined organic extracts were dried (Na$_2$SO$_4$) and concentrated in vacuo to give Ac-Hyp(OBzl)-OH as a white solid.

A solution of Ac-Hyp(OBzl)-OH (720 mg, 2.7 mmol) in MeOH (27 mL) was combined with 10% Pd/C (72 mg) and placed on a Parr hydrogenation apparatus under 50 psig H$_2$ for 16 h. The reaction mixture was filtered through diatomaceous earth and concentrated in vacuo to furnish 4a as a solid.

STEP b

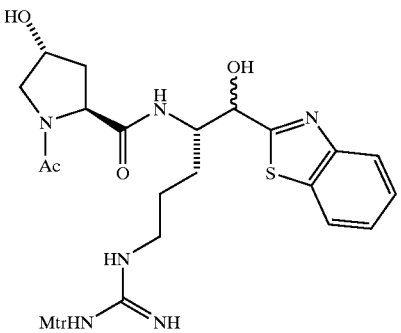

4b

A solution of 4a (230 mg, 1.32 mmol), 1-hydroxybenzotriazole (HOBT; 180 mg, 1.32 mmol), N,N-dimethylformamide (50 mL) was treated with 1,3-dicyclohexylcarbodiimide (DCC; 620 mg, 3.0 mmol) and the reaction mixture was stirred 16 h under argon. The reaction was diluted with water (150 mL), stirred for 1 h, and extracted with ethyl acetate (3×). The combine organic layers were extracted sequentially with water (3×), 1M aqueous KHSO$_4$, saturated aqueous NaHCO$_3$, brine, dried (Na$_2$SO$_4$) and concentrated in vacuo. The residue was purified by chromatography on silica gel eluting with CH$_2$Cl$_2$/MeOH (19:1) to give 4b as a white solid.

STEP c

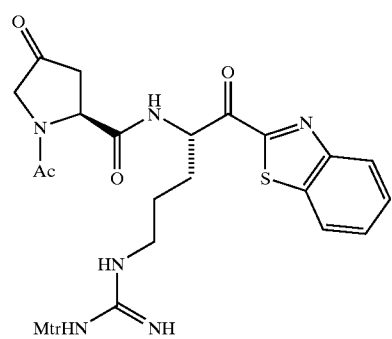

4c

Dess-Martin periodinane (373 mg, 0.88 mmol) was added to a solution of 4b (280 mg, 0.42 mmol) in CH$_2$Cl$_2$ (20 mL) while stirring under argon at room temperature. After 30 min, the reaction was quenched with a solution of 20% Na$_2$S$_2$O$_3$ (w/w) in saturated aqueous NaHCO$_3$ and the mixture was stirred at room temperature for 2 h. The organic layer separated and washed with brine, dried (Na$_2$SO$_4$), concentrated in vacuo. The residue was purified by chromatography on silica gel eluted with CH$_2$Cl$_2$/MeOH (39:1) to afford 4c as a white solid.

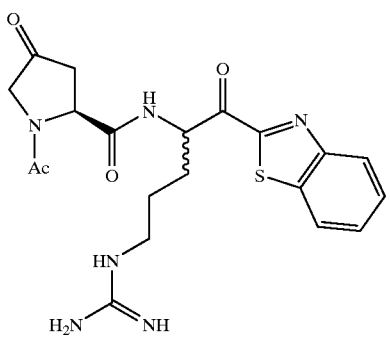

Compound 4

Compound 4c was deprotected and purified by reverse-phase HPLC by the procedure described in STEP i for Compound 3 to furnish Compound 4; MS (ES) m/z 445 (MH$^+$).

EXAMPLE 5

(2S,4R)-N-[4-[(aminoiminomethyl)amino]-1-(2-benzothiazolylcarbonyl)butyl]-4-hydroxy-1-methanesulfonyl-2-pyrrolidinecarboxamide STEP a

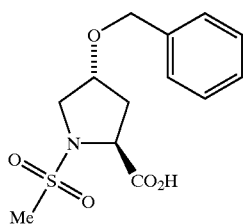

5a

Methanesulfonyl chloride (584 μL, 7.54 mmol) was added dropwise to a solution of 3e (2.05 g, 7.54 mmol), triethylamine (4.0 mL, 29 mmol) in CH$_2$Cl$_2$ (50 mL) at 0° C. while stirring under argon. The reaction was stirred for 30 min at 0° C., then 16 h at room temperature. The reaction mixture was filtered through diatomaceous earth, washed sequentially with 10% aqueous citric acid, saturated aqueous NaHCO$_3$, brine, dried (MgSO$_4$) and concentrated in vacuo to give an oil. Tetrahydrofuran (50 mL) was added followed by a solution of LiOH (474 mg, 11.3 mmol) in water (50 mL). The reaction was stirred for 60 min, concentrated in vacuo, acidified with 1N aqueous HCl, and extracted with CH$_2$Cl$_2$ (3×). The combined organic extracts were dried (MgSO$_4$) and concentrated in vacuo to give 5a as a white solid.

STEP b

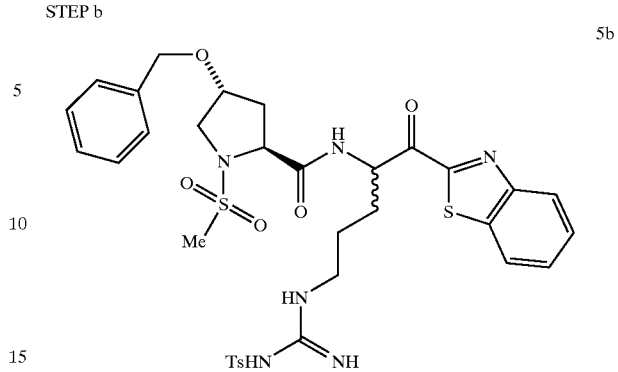

5b

A mixture of 5a (539 mg, 1.8 mmol), 1d (806 mg, 1.8 mmol), HOBt (240 mg, 1.8 mmol), in acetonitrile (50 mL) was treated with 1,3-dicyclohexylcarbodiimide (DCC; 900 mg, 3.6 mmol) and reaction stirred for 16 h at room temperature. The reaction was quenched with water, stirred for 1 h, and extracted with ethyl acetate (3×). The combined organic extracts were extracted with water (3×), 1M aqueous KHSO$_4$, saturated aqueous NaHCO$_3$, brine, dried (Na$_2$SO$_4$) and concentrated in vacuo. The residue was purified by chromatography on silica gel eluting with CH$_2$Cl$_2$/MeOH (19:1) to afford 5b as a white solid.

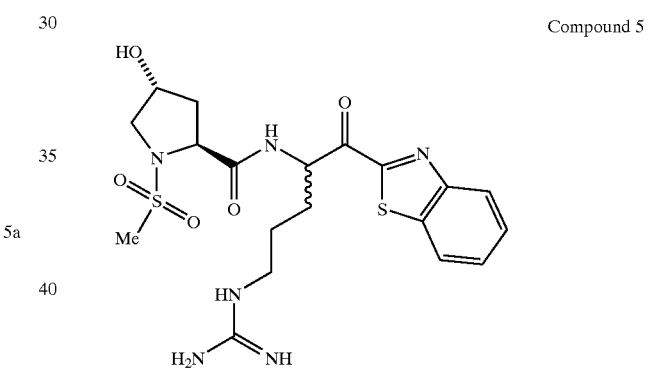

Compound 5

Compound 5b was converted to Compound 5 by methods analogous to those described in Example 1 with the exception that both arginine epimers were collected and combined to furnish Compound 5; MS (ES) m/z 483 (MH$^+$).

EXAMPLE 6

(2S)-N-[4-[(aminoiminomethyl)amino]-1-(2-benzothiazolylcarbonyl)butyl]-1-methanesulfonyl-2-pyrrolidinecarboxamide STEP a

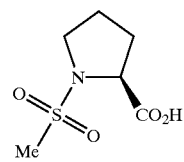

6a

Methanesulfonyl chloride (953 μL, 12.3 mmol) was added dropwise to a solution of L-proline tert-butyl ester (2.11 g, 12.3 mmol), triethylamine (3.4 mL, 24.6 mmol) in CH$_2$Cl$_2$ (50 mL) at 0° C. while stirring under argon. The reaction was stirred for 30 min at 0° C., filtered through diatomaceous earth, washed sequentially with 10% aqueous citric acid, saturated aqueous NaHCO₃, brine, dried (MgSO₄) and concentrated in vacuo. The residue was dissolved in a solution of trifluoroacetic acid/CH₂Cl₂ (1:1), stirred at room temperature for 30 min and concentrated in vacuo. The residue was triturated with hexanes (3×) and concentrated in vacuo to furnish 6a.

STEP b

Compound 6

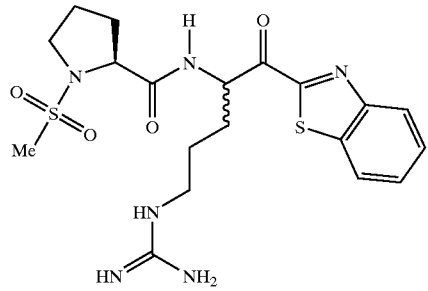

Compound 6 was prepared from 6a by methods analogous to those described in Example 1; MS (ES) m/z 467 (MH⁺).

EXAMPLE 7

(2S)-N-[4-[(Aminoiminomethyl)amino]-1-(2-benzothiazolylcarbonyl)butyl]-1-[(4-methylphenyl)sulfonyl]-2-pyrrolidinecarboxamide Compound 7

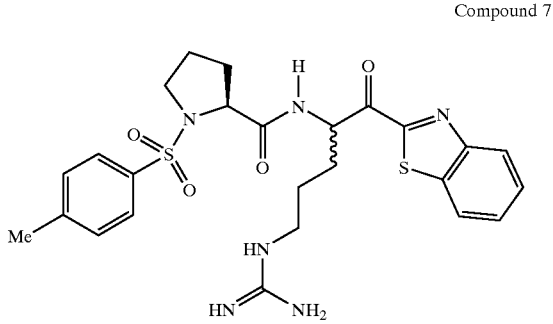

Compound 7 was prepared from N-p-toluenesulfonyl-L-proline by methods analogous to those described for Example 3; MS (ES) m/z 543 (MH⁺).

EXAMPLE 8

(2S)-trans-3-Acetyl-N-[4-[(aminoiminomethyl)amino]-1-(2-benzothiazolylcarbonyl)butyl]-3-azabicyclo(3.1.0)hexane-2-carboxamide Compound 8

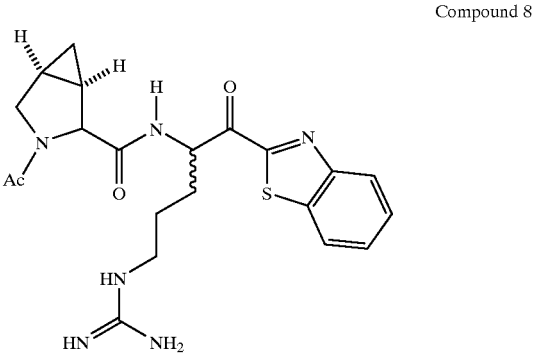

Compound 8 was prepared from trans-3-azabicyclo(3.1.0) hexane-2-carboxylic acid by methods analogous to those described in Example 3; MS (ES) m/z 443 (MH⁺).

EXAMPLE 9

(2S)-1-Acetyl-N-[4-[(aminoiminomethyl)amino]-1-(2-benzothiazolylcarbonyl)butyl]-2,3-dihydro-1H-indole-2-carboxamide Compound 9

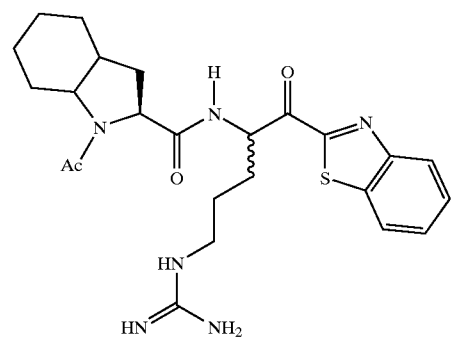

Compound 9 was prepared from octahydroindole-2-carboxylic acid by methods analogous to those described in Example 1 with the exception that both L- and D-arginine epimers were collected during the reverse-phase HPLC purification; MS (ES) m/z 485 (MH⁺).

EXAMPLE 10

(2S)-N-[4-[(aminoiminomethyl)amino]-1-(2-benzothiazolylcarbonyl)butyl]-1-(2-methyl-1-oxopropyl)-2-pyrrolidinecarboxamide Compound 10

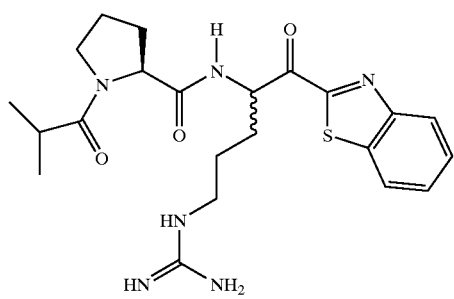

Compound 10 was prepared from L-proline methyl ester and isopropyl chloroformate by methods analogous to those described in Example 3; MS (ES) m/z 433 (MH+).

EXAMPLE 11

(2S)-N-[4-[(Aminoiminomethyl)amino]-1-(2-benzothiazolylcarbonyl)butyl]-1,2-pyrrolidinedicarboxamide, 1-methyl ester Compound 11

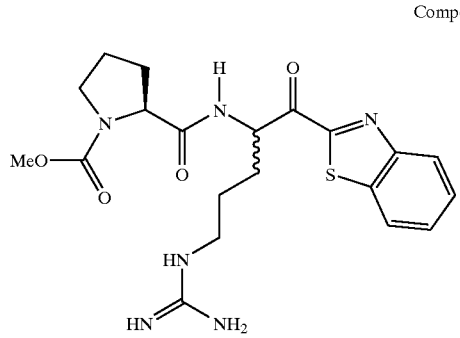

Compound 11 was prepared from L-proline methyl ester and methyl chloroformate by methods analogous to those described in Example 3; MS (ES) m/z 447 (MH+).

EXAMPLE 12

(3S)-1-Acetyl-N-[4-[(aminoiminomethyl)amino]-1-(2-benzothiazolylcarbonyl)butyl]-3-pyrrolidinecarboxamide Compound 12

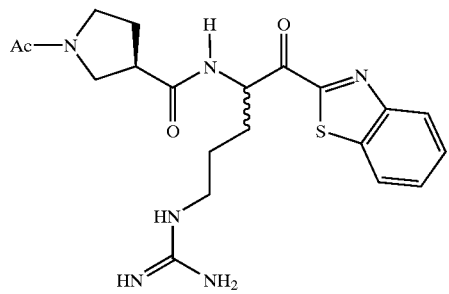

Compound 12 was prepared by methods analogous to those described in Example 3; MS (ES) m/z 431 (MH+).

EXAMPLE 13

(2S)-N-[4-[(Aminoiminomethyl)amino]-1-(2-benzothiazolylcarbonyl)butyl]-2-azetidinecarboxamide Compound 13

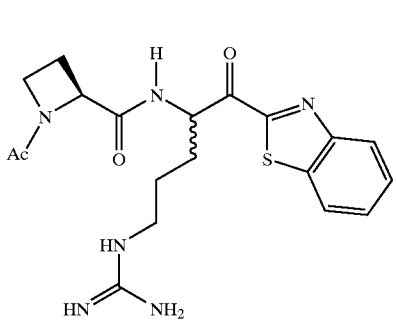

Compound 13 was prepared from (S)2-azetidineoarboxylic acid by methods analogous to those described in Example 3; MS (ES) m/z 417 (MH+).

EXAMPLE 14

(2S)-1-Acetyl-N-[4-[aminoiminomethyl)amino]-1-(2-benzothiazolylcarbonyl)butyl]-2-piperidinecarboxamide Compound 14

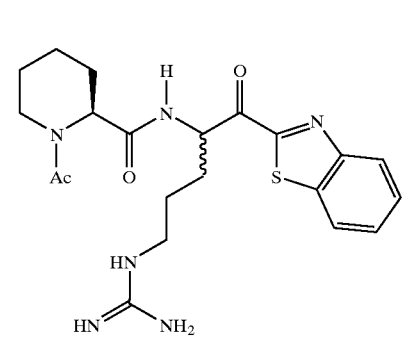

Compound 14 was prepared from N-acetyl-L-homoproline by methods analogous to those described in Example 1 with the exception that both arginine epimers were collected and combined to furnish Compound 14; MS (ES) m/z 445 (MH+).

EXAMPLE 15

(3S)-1-Acetyl-N-[4-[(aminoiminomethyl)amino]-1-(2-benzothiazolylcarbonyl)butyl]-3-piperidinecarboxamide Compound 15

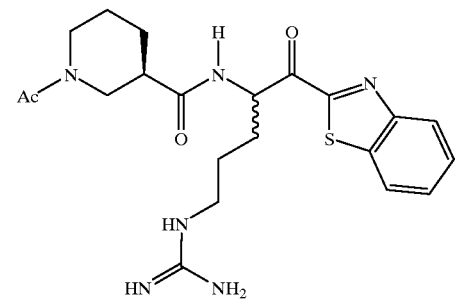

Compound 15 was prepared from ethyl (R)-nipecotate (CAS#25137-01-3) by methods analogous to those described in Example 3; MS (ES) m/z 445 (MH⁺).

EXAMPLE 16

N-[4-[(Aminoiminomethyl)amino]-1-(2-benzothiazolylcarbonyl)butyl]-1,2-cyclohexanedicarboxamide Compound 16

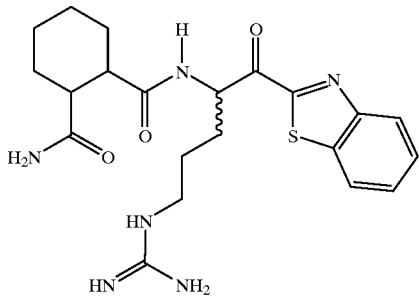

Compound 16 was prepared from 2-(aminocarbonyl)-cyclohexanecarboxylic acid by methods analogous to those described in Example 3; MS (ES) m/z 445 (MH⁺).

EXAMPLE 17

4-Acetamido-N-[4-[(aminoiminomethyl)amino]-1-(2-benzothiazolylcarbonyl)butyl]-cyclohexanecarboxamide Compound 17

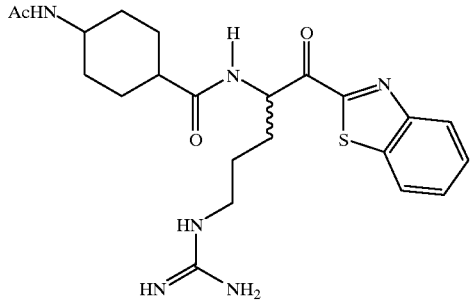

Compound 17 was prepared from 4-aminocyclohexanecarboxylic acid (CAS#1776-53-0) by methods analogous to those described in Example 3; MS (ES) m/z 459 (MH⁺).

EXAMPLE 18

(2S)-1-Acetyl-N-[4-[(aminoiminomethyl)amino]-1-(2-benzothiazolylcarbonyl)butyl]-2-pyrrolidinecarboxamide Compound 18

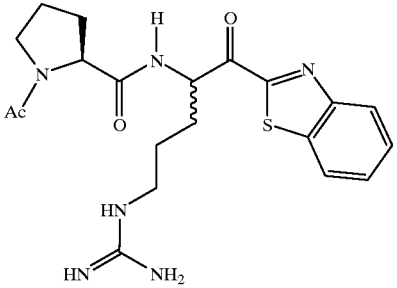

Compound 18 was prepared from N-acetyl-L-proline by methods analogous to those described in Example 3; MS (ES) m/z 431 (MH⁺).

EXAMPLE 19

(S)-3-Acetamido-N-[4-[(aminoiminomethyl)amino]-1-(2-benzothiazolylcarbonyl)butyl]-2-oxo-1-piperidineacetamide Compound 19

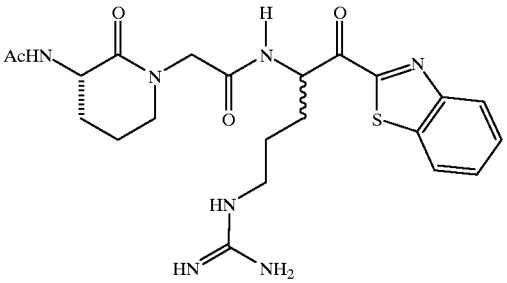

Compound 19 was prepared from (S)-3-amino-2-oxo-1-piperidineacetic acid (CAS#74411-98-6; see U.S. Pat. No. 4,192,875) by methods analogous to those described in Example 3; MS (ES) m/z 488 (MH⁺).

EXAMPLE 20

1-Acetyl-N-[4-[(aminoiminomethyl)amino]-1-(2-benzothiazolylcarbonyl)butyl]4-piperidineacetamide Compound 20

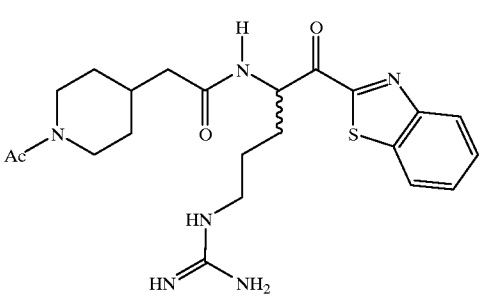

Compound 20 was prepared from 4-piperidineacetic acid (CAS#51052-78-9) by methods analogous to those described in Example 3; MS (ES) m/z 459 (MH+).

EXAMPLE 21

2-(Acetyimethylamino)-N-[4-[(aminoiminomethyl)amino]-1-(2-benzothiazolylcarbonyl)butyl]acetamide

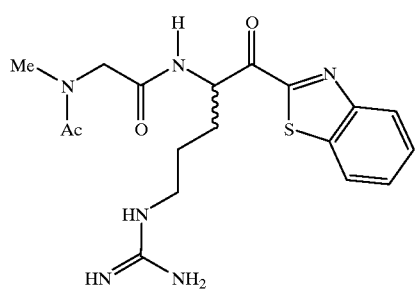

Compound 21

Compound 21 was prepared from N-acetylsarcosine by methods analogous to those described in Example 3; MS (ES) m/z 405 (MH+).

EXAMPLE 22

2-(Acetylamino)-N-[4-[(aminoiminomethyl)amino]-1-(2-benzothiazolylcarbonyl)butyl]acetamide

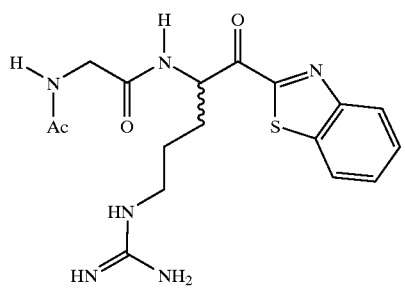

Compound 22

Compound 22 was prepared from N-acetylglycine by methods analogous to those described in Example 3; MS (ES) m/z 391 (MH+).

EXAMPLE 23

N-[4-[(Aminoiminomethyl)amino]-1-(2-benzothiazolylcarbonyl)butyl]butanediamide

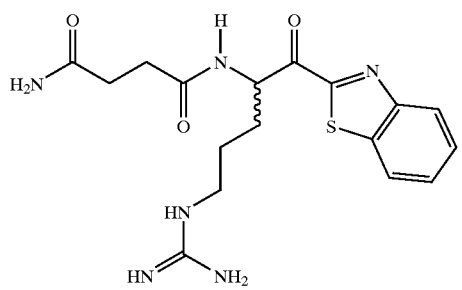

Compound 23

Compound 23 was prepared from succinamic acid by methods analogous to those described in Example 3; MS (ES) m/z 391 (MH+).

EXAMPLE 24

(2S,4R)-1-Acetyl-N-[4-[(aminoiminomethyl)amino]-1-(2-thiazolylcarbonyl)butyl]-4-hydroxy-2-pyrrolidinecarboxamide

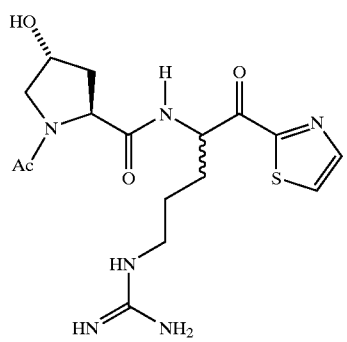

Compound 24

Compound 24 was prepared from trans-1-acetyl-4-benzyloxy-L-proline by methods analogous to those described in Example 1 with the exception that thiazole was used instead of benzothiazole and that both L- and D-arginine epimers were collected during the reverse-phase HPLC purification; MS (ES) m/z 397 (MH+).

EXAMPLE 25

(2S,4R)-1-Acetyl-N-[1-(2-benzothiazolylcarbonyl)-5-(methylamino)pentyl]-4-hydroxy-2-pyrrolidinecarboxamide

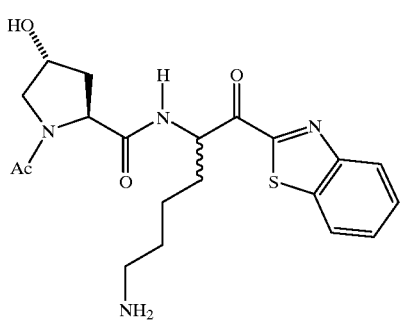

Compound 25

Compound 24 was prepared from trans-1-acetyl-4-benzyloxy-L-proline by methods analogous to those described in Example 1 with the exception that N-α-t-Boc-N-ε-(4-methoxy-2,3,6-trimethylbenzenesulfonyl)-L-lysine (Boc-Lys(Mtr)-OH) was used instead of N-αt-Boc-N$^G$-(p-toluenesulfonyl)-L-arginine (Boc-Arg(Ts)-OH) and that both L- and D-arginine epimers were collected during the reverse-phase HPLC purification; MS (ES) m/z 397 (MH+).

EXAMPLE 26

N-(1-Oxo-2-propylpentyl)-L-α-aspartyl-N-[4-[(aminoiminomethyl)amino]-1-(2-benzothiazolylcarbonyl)butyl]-L-prolinamide, methyl ester Compound 26

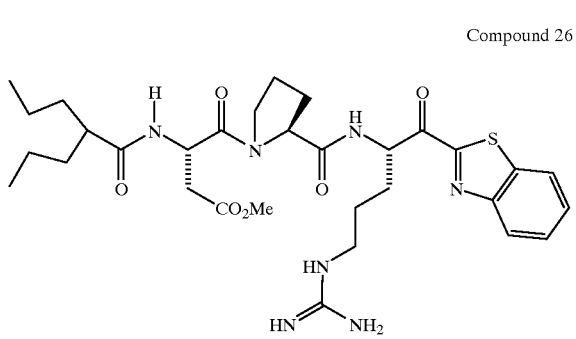

Compound 26 is prepared from 4-methyl-N-(1-oxo-2-propylpentyl)-L-α-aspartyl-L-proline (CAS#151275-35-3; see WO 9315756) by methods analogous to those described in Example 1; MS (ES) m/z 644 (MH+).

EXAMPLE 27

N-(Carboxymethyl)-3-cyclohexyl-D-alanyl-N-[(1S)-4-[(aminoiminomethyl)amino]-1-(2-benzothiazolylcarbonyl)butyl]-L-prolinamide Compound 27

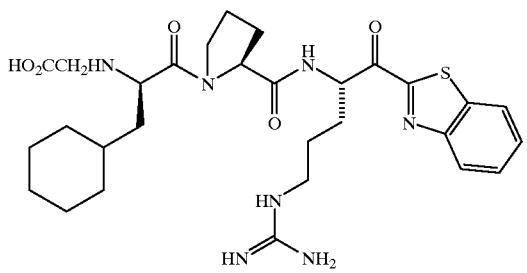

N-[2-(1,1-dimethylethoxy)-2-oxoethyl]-D-phenylalanine is prepared by the method use to prepare the corresponding L-epimer, N-[2-(1,1-dimethylethoxy)-2-oxoethyl]-L-phenylalanine (CAS#166108-57-2; see *Biomed. Pept., Proteins Nucleic Acids* 1994, Vol. 1(1), pp. 51–56). N-[2-(1,1-dimethylethoxy)-2-oxoethyl]-D-phenylalanine is converted to Compound 27 by methods analogous to those described in Example 1; MS (ES) m/z 600 (MH+).

EXAMPLE 28

(3S)-N-[(1S)-4-[(Aminoiminomethyl)amino]-1-(2-benzothiazolylcarbonyl)butyl]hexahydro-2-oxo-3-[[(phenylmethyl)sulfonyl]amino]-1H-azepine-1-acetamide Compound 28

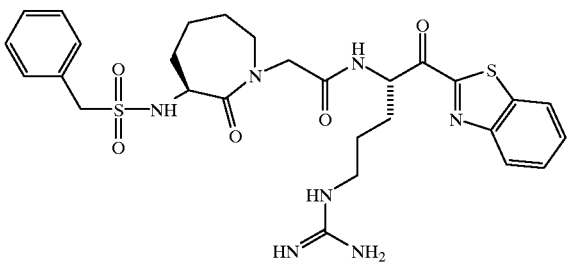

Compound 28 is prepared from (3S)-hexahydro-2-oxo-3-[[(phenylmethyl)sulfonyl]amino]-1H-azepine-1-acetic acid, (9Cl) (CAS#174960-90-8; see WO 9535311) by methods analogous to those described in Example 1; MS (ES) m/z 614 (MH+).

EXAMPLE 29

STEP a

Compound 29a

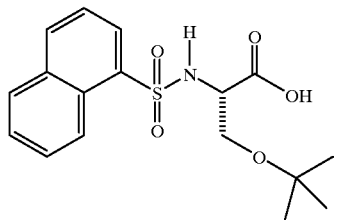

A solution of O-tert-butyl-L-serine (2.0 g, 11.7 mmol), triethylamine (5.2 mL, 37.3 mmol) in CH$_2$Cl$_2$ (100 mL) was cooled to 0° C. and while stirring under argon. 1-Naphthalenensulfonyl chloride (4.0 g, 17.6 mmol) was added and the reaction was slowly warmed to room temperature over 18 h, extracted with 1 N aqueous HCl (3×), brine, dried MgSO$_4$, and concentrated in vacuo. The residue was purified on silica gel eluting with ethyl acetate/hexanes/acetic acid (60:40:1) to afford 29a.

STEP b

Compound 29b

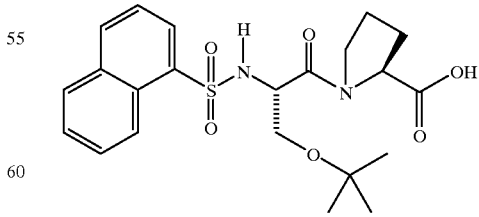

A mixture of 29a (3.93 g, 11.1 mmol), L-proline benzyl ester hydrochloride (4.02 g, 16.6 mmol), 1-hydroxybenzotriazole (HOBT; 2.24 g, 16.6 mmol) and triethylamine (5.0 mL, 35.9 mmol) in acetonitrile (50 mL)

was treated with 1,3-dicyclohexylcarbodiimide (DCC; 4.60 g, 22.2 mmol) while stirring at room temperature under argon. After 18 h, the reaction mixture was filtered through diatomaceous earth and concentrated in vacuo. The residue was partitioned between water and ethyl acetate. The aqueous layer was extracted with ethyl acetate (3×). The combined organic extracts were extracted with saturated aqueous NaHCO₃ (3×), brine, dried (Na₂SO₄) and concentrated in vacuo. The residue was purified by chromatography on silica gel eluting with hexanes/ethyl acetate (7:3) to furnish 29b.

Step c

N-(1-Naphthylsulfonyl)-L-seryl-N-[4-[(aminoiminomethyl)amino]-1-(2-benzothiazolylcarbonyl)butyl]-L-prolinamide Compound 29

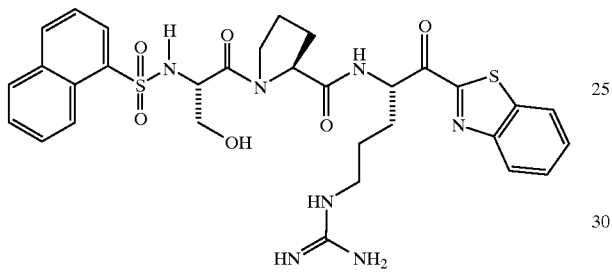

Compound 29 is prepared from 29b by methods analogous to those described in Example 1; MS (ES) m/z 666 (MH⁺).

EXAMPLE 30

N-Methyl-D-phenylalanyl-N-[(2S)-[1-(aminoiminomethyl)-3-piperidinyl]-1-(2-benzothiazolylcarbonyl)ethyl]-L-prolinamide Compound 30a

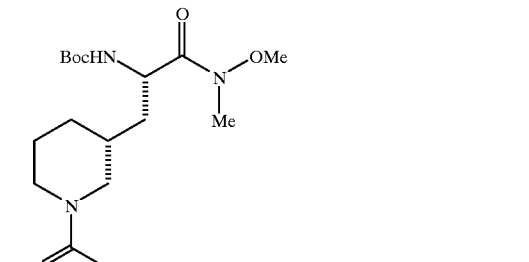

Compound 30a was prepared using tosyl chloride instead of Mtr chloride by the method described for (S)-[1-[[1-[imino[[(4-methoxy-2,3,6-trimethylphenyl)-suflonyl]amino]methyl]-4-piperidinyl]methyl]-2-(methoxymethylamino)-2-oxoethyl]carbamic acid, 1,1-dimethylethyl ester (CAS#201007-52-5; see WO 9748687, Example 7).

Compound 30

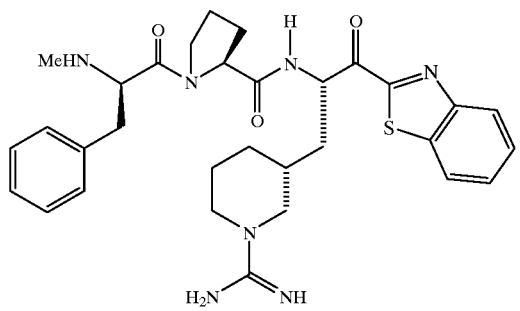

Compound 30 was prepared from Compound 30a by methods analogous to those described for Example 57 in U.S. Pat. No. 523,308; MS (ES) m/z 590 (MH⁺).

EXAMPLE 31

(S)-N-methyl-D-phenylalanyl-N-[1-[[3-(aminoiminomethyl)phenyl]methyl]-2-(2-benzothiazolyl)-2-oxoethyl]-L-prolinamide Compound 31

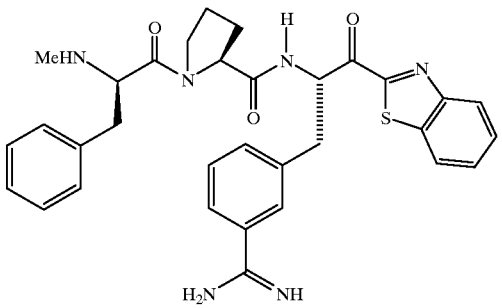

Compound 31 was prepared from N-[(1,1-dimethylethoxy)carbonyl]-3-[imino[[(4-methoxy-2,3,6-trimethylphenyl)sulfonyl]amino]methyl]-phenylalanine (CAS#174894-05-4; see WO 9535312) by methods analogous to those described for Example 57 in U.S. Pat. No. 523,308; MS (ES) m/z 583 (MH⁺).

EXAMPLE 32

(S)-N-[1-[[3-(Aminoiminomethyl)phenyl]methyl]-2-(2-benzothiazolyl)-2-oxoethyl]-α-(acetylamino)cyclohexanepropanamide Compound 32

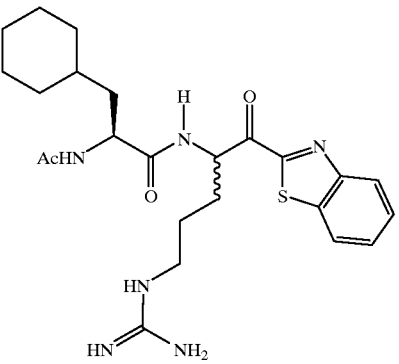

Compound 32 was prepared from N-acetyl-L-cyclohexylalanine by methods analogous to those described for Example 3; MS (ES) m/z 487 (MH+).

EXAMPLE 33

(S)-2-(Acetylamino)-N-[1-[[3-(aminoiminomethyl)phenyl]methyl]-2-(2-benzothiazolyl)-2-oxoethyl]-3-methyl-butanamide Compound 33

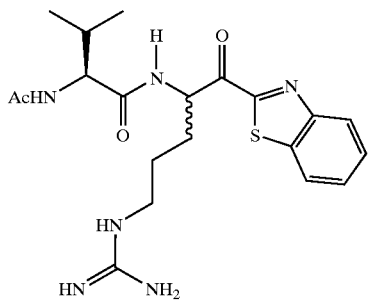

Compound 33 was prepared from N-acetyl-L-valine by methods analogous to those described for Example 3; MS (ES) m/z 433 (MH+).

EXAMPLE 34

(2S)-N-[1-[[3-(Aminoiminomethyl)phenyl]methyl]-2-(2-benzothiazolyl)-2-oxoethyl]-1-benzoyl-2-pyrrolidinecarboxamide Compound 34

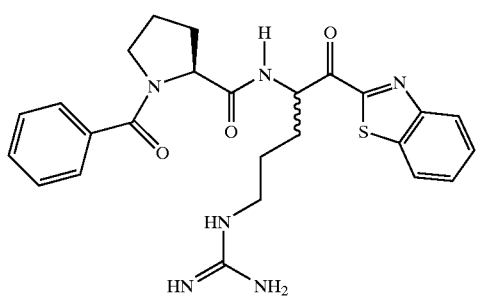

Compound 34 was prepared by methods analogous to those described for Example 3; MS (ES) m/z 493 (MH+).

EXAMPLE 35

N-[1-[[3-(Aminoiminomethyl)phenyl]methyl]-2-(2-benzothiazolyl)-2-oxoethyl]-2-pyridinecarboxamide STEP a 35a

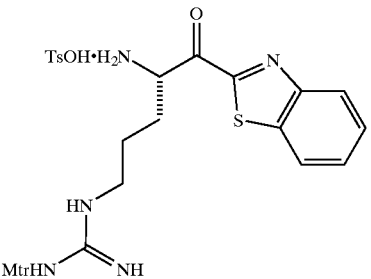

A solution of 3b (5.00 g, 8.28 mmol) in a minimum amount of $CH_2Cl_2$ was treated with p-toluenesulfonic acid monohydrate ($TsOH \cdot H_2O$; 3.93 g, 20.7 mmol). Additional $CH_2Cl_2$ was added until complete solution was effected. The resulting solution and stirred over 16 h under nitrogen at room temperature. The reaction was concentrated to about 5 mL and immediately used in STEP b.

STEP b

Compound 35b

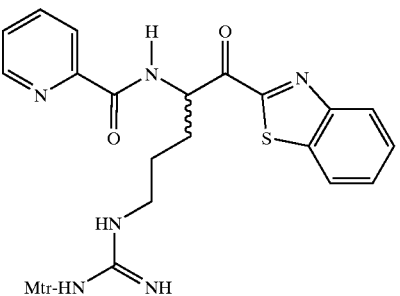

A solution of 2-pyridinecarboxylic acid (2.04 g, 16.6 mmol) and 1-hydroxybenzotriazole (HOBT; 4.48 g, 33.1 mmol) in dry acetonitrile (20 mL) was treated 1,3-dicyclohexylcarbodiimide (DCC; 10.25 g, 49.7 mmol) with while stirring under nitrogen at room temperature. After 15 min, the $CH_2Cl_2$ solution of 35a was added and the resulting mixture was stirred for 18 h. The reaction was quenched with water (300 mL), stirred for 1 h, filtered through diatomaceous earth, and the acetonitrile was removed in vacuo. The resulting aqueous layer was extracted with ethyl acetate (2×). The combined organic extracts were extracted with 1M $KHSO_4$, combined with saturated aqueous $NaHCO_3$ and stirred for 2 h at room temperature. The layers were separated and the organic extracts were washed with brine, dried ($Na_2SO_4$), and concentrated in vacuo to afford 35b.

STEP c

Compound 35

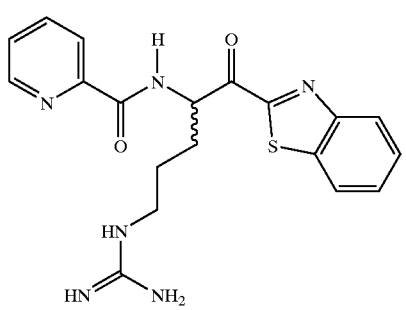

Compound 35 was prepared by deprotecting and purifying 35b via the method described for Example 3; MS (ES) m/z 494 (MH$^+$).

EXAMPLE 36

(2S)-N-[4-[(Aminoiminomethyl)amino]-1-(2-benzothiazolylcarbonyl)butyl]-1,2-pyrrolidinedicarboxamide, 1-N,N-dimethylamide Compound 36

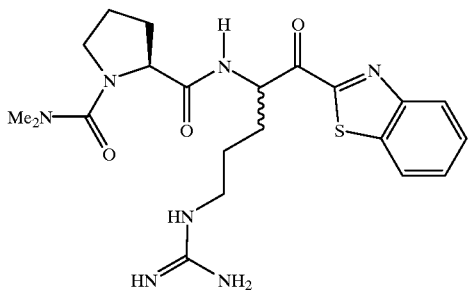

Compound 36 is prepared from L-proline methyl ester and dimethylcarbamoyl chloride by methods analogous to those described for Example 3.

EXAMPLE 37

(2S)-1-Acetyl-N-[4-[(aminoiminomethyl)amino]-1-(2-benzothiazolylcarbonyl)butyl]-3,4-dehydro-2-pyrrolidinecarboxamide Compound 37

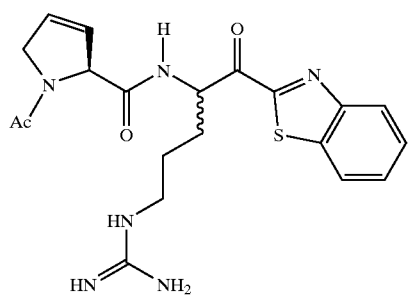

Compound 37 was prepared from 3,4-dehydro-L-proline methyl ester by methods analogous to those described for Example 3; MS (ES) m/z 429 (MH$^+$).

EXAMPLE 38

2-(Acetylcyclhexylamino)-N-[4-[(aminoiminomethyl)amino]-1-(2-benzothiazolylcarbonyl)butyl]acetamide Compound 38

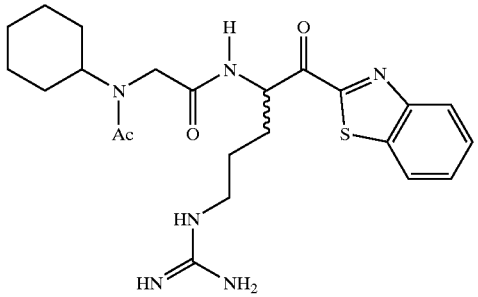

Compound 38 was prepared from cyclohexylglycine (CAS#58695-41-3; see EP 187130) by methods analogous to those described for Example 3; MS (ES) m/z 473 (MH$^+$).

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the formula I:

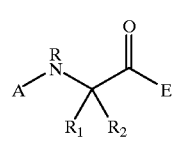

(I)

wherein:

A is selected from the group consisting of

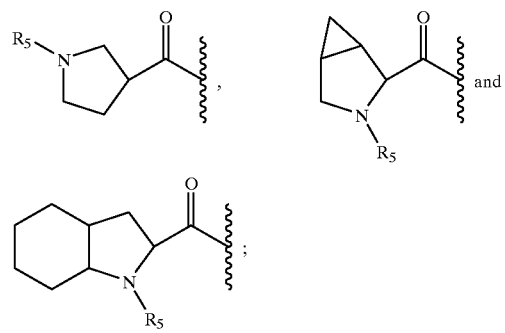

a D or L amino acid which is coupled at its carboxy terminus to the nitrogen depicted in formula (I) and is selected from the group consisting of dehydroproline, proline, substituted proline (where the the substituents on the proline are independently selected from one or more of $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, phenylalkyloxy, phenyl or $C_{1-4}$alkoxycarbonyl),
  where the amino terminus of said amino acid is connected to a member selected from the group consisting of [1,2,3,4]-tetrahydroisoquinoline-1-carbonyl, [1,2,3,4]-tetrahydroisoquinoline-3-carbonyl, formyl, $C_{1-4}$alkoxycarbonyl, $C_{1-8}$alkylcarbonyl, perfluoro$C_{1-4}$alkylsulfonyl, $C_{1-4}$alkylsulfonyl, amido, N—$C_{1-4}$alkylamido, N,N—$C_{1-4}$dialkylamido, sulfonamido, arylsulfonyl, substituted arylsulfonyl (where the aryl substituents are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), camphorsulfonyl, $C_{1-4}$alkylsulfinyl, arylsulfinyl, substituted arylsulfinyl (where the aryl substituents are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), and arylcarbonyl; or
a poly peptide comprised of two amino acids,
  where the first amino acid is a D or L amino acid, bound via its carboxy terminus to the nitrogen depicted in formula (I) and is selected from the group consisting of proline and substituted proline (where the the substituents on the proline are independently selected from one or more of $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, aralkyloxy, aryl or $C_{1-4}$alkoxycarbonyl),
  and the second D or L amino acid, is bound to the amino terminus of said first amino acid, and is selected from the group consisting of aspartic acid, aspartic acid-4-$C_{1-4}$alkyl ester, glutamic acid, glutamic acid-5-$C_{1-4}$alkyl ester, serine, phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine,
  where the amino terminus of said second amino acid is monosubstituted with a member of the group consisting of $C_{1-6}$alkyl, carboxy$C_{1-8}$alkyl, and $C_{1-10}$alkylcarbonyl;
R, and $R_1$ are each independently selected from the group consisting of hydrogen and $C_{1-5}$alkyl;
$R_2$ is
  selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{25}$alkyl, $C_{1-3}$alkoxy$C_{2-5}$alkyl, phenyl, substituted phenyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), benzyl, substituted benzyl (where the substituents on the benzyl are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl$C_{1-4}$alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl;
$R_5$ is
  selected from the group consisting of hydrogen, $C_{1-4}$alkyl and $C_{1-4}$alkylcarbonyl;
E is
  an unsubstituted or substituted heterocycle selected from the group consisting of imidazolin-2-yl, imidazol-2-yl, oxazolin-2-yl, oxazol-2-yl, thiazolin-2-yl, thiazol-2-yl, thiazol-5-yl, 1,3,4-thiadiazol-2-yl, 1,2,4-thiadiazol-3-yl, 1,2,4-thiadiazol-5-yl, isothiazol-3-yl, 1,2,3-triazol-4-yl, 1,2,3-triazol-5-yl, tetrazol-5-yl, isoxazol-3-yl, 1,2,3,4-oxatriazol-5-yl, 1,2,3-oxadiazol-4-yl, 1,3,4-oxadiazol-2-yl, 1,2,4-oxadiazol-3-yl, 1,3,4-oxadiazol-2-yl, 2-pyrazolin-3-yl, pyrazol-3-yl, 1H-indazole-3-yl, benzoxazol-2-yl, benzimidazol-2-yl, benzothiazol-2-yl, 4,5,6,7-tetrahydro-benzothiazol-2-yl, wherein the substituents on the heterocycle are independently selected from $C_{1-4}$alkyl, perfluoro $C_{1-4}$alkyl, $C_{1-4}$alkoxy, hydroxy, halo, amido, nitro, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkoxycarbonyl, phenyl$C_{1-4}$alkylaminocarbony, aryl, or substituted aryl where the substituents on the aryl are independently selected from one or more of $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl;

provided that when

A is a polypeptide wherein the first amino acid is unsubstituted proline, and the second amino acid is selected from the group consisting of aspartic acid, aspartic acid-4-$C_{1-4}$alkyl ester, glutamic acid, glutamic acid-5-$C_{1-4}$alkyl ester, phenylalanine, substituted phenylalanine (where the phenyl substituents are independently selected from one or more of, $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine, where the amino terminus of said second amino acid is monosubstituted with a member of the group consisting of $C_{1-6}$alkyl, carboxy$C_{1-8}$alkyl, and $C_{1-10}$alkylcarbonyl;

then $R_2$ is selected from the group consisting of substituted phenyl (where the substituents are independently selected from one or more of amidino, hydrazino, amidrazonyl), substituted benzyl (where the substituents on the benzyl are independently selected from one or more of hydrazino, amidrazonyl), pyridyl, substituted pyridyl (where the substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl$C_{1-4}$ alkyl, substituted pyrimidyl$C_{1-4}$alkyl (where the pyrimidine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), triazin-2-yl-$C_{1-4}$alkyl, substituted triazin-2-yl-$C_{1-4}$alkyl (where the triazine substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently selected from one or more of amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, and N-amidinopiperazinyl-N—$C_{0-4}$alkyl;

and pharmaceutically acceptable salts and prodrugs thereof.

2. The compound of claim 1 wherein:

A is
selected from the group consisting of

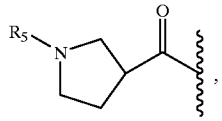, 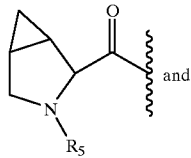 and

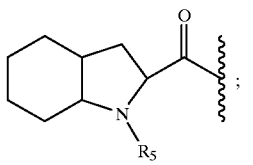;

a D or L amino acid which is coupled at its carboxy terminus to the nitrogen depicted in formula (I) and is selected from the group consisting of dehydroproline, proline, substituted proline (where the the substituents on the proline are independently one to three substituents selected from $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, phenylalkyloxy, phenyl or $C_{1-4}$alkoxycarbonyl), where the amino terminus of said amino acid is connected to a member selected from the group consisting of formyl, $C_{1-4}$alkoxycarbonyl, $C_{1-8}$alkylcarbonyl, perfluoro$C_{1-4}$alkylsulfonyl, $C_{1-4}$alkylsulfonyl, amido, N—$C_{1-4}$alkylamido, N,N—$C_{1-4}$dialkylamido, sulfonamido, arylsulfonyl, substituted arylsulfonyl (where the aryl substituents are independently one to three substituents selected from $C_{1-4}$alkyl, perfluoro $C_{1-4}$alkyl, $C_{1-4}$alkoxy, hydroxy, halo, amido, N—$C_{1-4}$alkylamido, N,N—$C_{1-4}$dialkylamido, nitro, amino, $C_{1-4}$alkylamino, $C_{1-4}$dialkylamino, carboxy, or $C_{1-4}$alkoxycarbonyl), and arylcarbonyl; or a poly peptide comprised of two amino acids,
where the first amino acid is a D or L amino acid, bound via its carboxy terminus to the nitrogen depicted in formula (I) and is selected from the group consisting of proline and substituted proline (where the the substituents on the proline are independently one to three substituents selected from $C_{1-4}$alkyl, perfluoro $C_{1-4}$alkyl, $C_{1-4}$alkoxy, hydroxy, oxo, halo, amido, N—$C_{1-4}$alkylamido, N,N—$C_{1-4}$dialkylamido, nitro, amino, $C_{1-4}$alkylamino, $C_{1-4}$dialkylamino, carboxy, $C_{1-4}$alkylcarbonyloxy, phenylalkyloxy, phenyl or $C_{1-4}$alkoxycarbonyl), and the second D or L amino acid, is bound to the amino terminus of said first amino acid, and is selected from the group consisting of aspartic acid, aspartic acid-4-$C_{1-4}$alkyl ester, glutamic acid, glutamic acid-5-$C_{1-4}$alkyl ester, serine, phenylalanine, substituted phenylalanine (where the phenyl substituents are independently one to three substituents selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine, where the amino terminus of said second amino acid is monosubstituted with a member of the group consisting of $C_{1-6}$alkyl, carboxy$C_{1-8}$alkyl, and $C_{1-10}$alkylcarbonyl;

R is hydrogen; and $R_2$ is
selected from the group consisting of amino$C_{2-5}$alkyl, guanidino$C_{2-5}$alkyl, $C_{1-4}$alkylguanidino$C_{2-5}$alkyl, di$C_{1-4}$alkylguanidino-$C_{2-5}$alkyl, amidino$C_{2-5}$alkyl, $C_{1-4}$alkylamidino$C_{2-5}$alkyl, di$C_{1-4}$alkylamidino$C_{2-5}$alkyl, $C_{1-3}$alkoxy$C_{2-5}$alkyl, phenyl, substituted phenyl (where the substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), benzyl, substituted benzyl (where the substituents on the benzyl are independently one to three substituents selected from amino, amidino, guanidino, hydrazino, amidrazonyl, $C_{1-4}$ alkylamino, $C_{1-4}$dialkylamino, halogen, perfluoro $C_{1-4}$alkyl, $C_{1-4}$alkyl, $C_{1-3}$alkoxy or nitro), pyridyl, substituted pyridyl (where the substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl$C_{1-4}$alkyl, substituted pyrimidyl$C_{1-4}$alkyl (where the pyrimidine substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, N-amidinopiperazinyl-N—$C_{0-4}$alkyl, hydroxy$C_{2-5}$alkyl, $C_{1-5}$alkylamino$C_{2-5}$alkyl, $C_{1-5}$dialkylamino$C_{2-5}$alkyl, N-amidinopiperidinyl$C_{1-4}$alkyl and 4-aminocyclohexyl$C_{0-2}$alkyl;

provided that when

A is a polypeptide wherein the first amino acid is unsubstituted proline, and the second amino acid is selected from the group consisting of aspartic acid, aspartic acid-4-$C_{1-4}$alkyl ester, glutamic acid, glutamic acid-5-$C_{1-4}$alkyl ester, phenylalanine, substituted phenylalanine (where the phenyl substituents are independently one to three substituents selected from $C_{1-4}$alkyl, perfluoro$C_{1-4}$alkyl, $C_{1-4}$alkoxy, hydroxy, halo, amido, nitro, amino, $C_{1-4}$alkylamino, $C_{1-4}$dialkylamino, carboxy or $C_{1-4}$alkoxycarbonyl), cyclohexylglycine, and cyclohexylalanine, where the amino terminus of said second amino acid is monosubstituted with a member of the group consisting of $C_{1-6}$alkyl, carboxy$C_{1-8}$alkyl, and $C_{1-10}$alkylcarbonyl;

then $R_2$ is selected from the group consisting of substituted phenyl (where the substituents are independently one to three substituents selected from amidino, hydrazino, amidrazonyl), substituted benzyl (where the substituents on the benzyl are independently one to three substituents selected from hydrazino, amidrazonyl), pyridyl, substituted pyridyl (where the substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyridyl$C_{1-4}$alkyl, substituted pyridyl$C_{1-4}$alkyl (where the pyridine substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), pyrimidyl$C_{1-4}$alkyl, substituted pyrimidyl$C_{1-4}$alkyl (where the pyrimidine substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazo$C_{1-4}$alkyl, substituted imidazo$C_{1-4}$alkyl (where the imidazole substituents are independently one to three substituents selected from amino, amidino, guanidino, hydrazino, amidrazonyl, $C_{1-4}$alkylamino, $C_{1-4}$dialkylamino, halogen, perfluoro $C_{1-4}$alkyl, $C_{1-4}$alkyl, $C_{1-3}$alkoxy or nitro), imidazolinyl$C_{1-4}$alkyl, and N-amidinopiperazinyl-N—$C_{0-4}$alkyl;

and pharmaceutically acceptable salts and prodrugs thereof.

3. The compound of claim 2 wherein

A is selected from the group consisting of

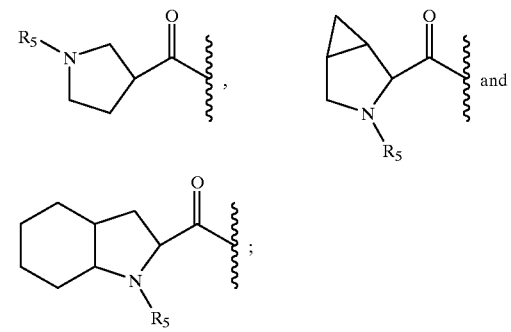

a D or L amino acid which is coupled at its carboxy terminus to the nitrogen depicted in formula (I) and is selected from the group consisting of dehydroproline, proline, substituted proline (where the the substituents on the proline are independently one to two substituents selected from $C_{1-4}$alkyl, hydroxy, oxo, halo, amido, phenylalkyloxy, or $C_{1-4}$alkoxy), pipecolinic acid, where the amino terminus of said amino acid is connected to a member selected from the group consisting of $C_{1-4}$alkoxycarbonyl, $C_{1-8}$alkylcarbonyl, $C_{1-4}$alkylsulfonyl, amido, N—$C_{1-4}$alkylamido, N,N—$C_{1-4}$dialkylamido, sulfonamido, arylcarbonyl, arylsulfonyl, and substituted arylsulfonyl (where the aryl substituents are independently one to two substituents selected from $C_{1-4}$alkyl, or perfluoro $C_{1-4}$alkyl);

$R_1$ is selected from the group consisting of hydrogen and methyl;

$R_2$ is selected from the group consisting of amino$C_{2-5}$alkyl or guanidino$C_{2-5}$alkyl; and E is an unsubstituted or substituted heterocycle selected from the group consisting of imidazol-2-yl, oxazolin-2-yl, oxazol-2-yl, thiazol-2-yl, benzoxazol-2-yl, benzimidazol-2-yl, benzothiazol-2-yl, 4,5,6,7-tetrahydro-benzothiazol-2-yl, wherein the substituents on the heterocycle are independently one or two substituents selected from $C_{1-4}$alkyl, perfluoro $C_{1-4}$alkyl, $C_{1-4}$alkoxy, hydroxy, halo, amido, N—$C_{1-4}$ alkylamido, N,N—$C_{1-4}$dialkylamido, carboxy or $C_{1-4}$alkoxycarbonyl;

and pharmaceutically acceptable salts and prodrugs thereof.

4. The compound of claim 3 wherein

A is
selected from the group consisting of proline and substituted proline (where the substituent is one or two substituents independently selected from hydroxy, halo or oxo);

$R_2$ is
selected from the group consisting of amino$C_{2-5}$alkyl and guanidino$C_{2-5}$alkyl; and, E is
an unsubstituted heterocycle selected from the group consisting of imidazol-2-yl, oxazol-2-yl, thiazol-2-yl, benzoxazol-2-yl, benzimidazol-2-yl or benzothiazol-2-yl;

and pharmaceutically acceptable salts and prodrugs thereof.

5. The compound of claim 4 wherein:
A is mono-substituted proline where the substituent is selected from hydroxy, halo or oxo;
$R_1$ is hydrogen;
$R_2$ is guanidino$C_{2-5}$alkyl; and
E is benzothiazol-2-yl;
and pharmaceutically acceptable salts and prodrugs thereof.

6. A compound selected from
(2S,4R)-1-Acetyl-N-[(1S)-4-[(aminoiminomethyl)amino]-1-(2-benzothiazolylcarbonyl)butyl]-4-hydroxy-2-pyrrolidinecarboxamide;
(2S,4R)-1-Acetyl-N-[4-[(aminoiminomethyl)amino]-1-(2-benzothiazolylcarbonyl)butyl]-4-hydroxy-2-pyrrolidinecarboxamide;
(2S)-1-Acetyl-N-[4-[(aminoiminomethyl)amino]-1-(2-benzothiazolylcarbonyl)butyl]-4-oxo-2-pyrrolidinecarboxamide;
(2S,4R)-N-[4-[(aminoiminomethyl)amino]-1-(2-benzothiazolylcarbonyl)butyl]-4-hydroxy-1methanesulfonyl-2-pyrrolidinecarboxamide;
(2S)-N-[4-[(aminoiminomethyl)amino]-1-(2-benzothiazolylcarbonyl)butyl]-1-methanesulfonyl-2-pyrroli dinecarboxamide;
(2S)-N-[4-[(Aminoiminomethyl)amino]-1-(2-benzothiazolylcarbonyl)butyl]-1-[(4-methylphenyl)sulfonyl]-2-pyrrolidinecarboxamide;
(2S)-trans-3-Acetyl-N-[4-[(aminoiminomethyl)amino]-1-(2-benzothiazolylcarbonyl)butyl]-3-azabicyclo(3.1.0)hexane-2-carboxamide;
(2S)-1-Acetyl-N-[4-[(aminoiminomethyl)amino]-1-(2-benzothiazolyl-carbonyl)butyl]-2,3-dihydro-1H-indole-2-carboxamide;
(2S)-N-[4-[(aminoiminomethyl)amino]-1-(2-benzothiazolylcarbonyl)butyl]-1-(2-methyl-1-oxopropyl)-2-pyrrolidinecarboxamide;
(2S)-N-[4-[(Aminoiminomethyl)amino]-1-(2-benzothiazolylcarbonyl)butyl]-1,2-pyrrolidinedicarboxamide, 1-methyl ester;
(3S)-1-Acetyl-N-[4-[(aminoiminomethyl)amino]-1-(2-benzothiazolylcarbonyl)butyl]-3-pyrrolidinecarboxamide;
(2S)-N-[4-[(Aminoiminomethyl)amino]-1-(2-benzothiazolylcarbonyl)butyl]-2-azetidinecarboxamide;
(2S,4R)-1-Aetyl-N-[4-[(aminoiminomethyl)amino]-1-(2-thiazolylcarbonyl)butyl]-4-hydroxy-2-pyrroldinecarboxamide;
(2S,4R)-1-Acetyl-N-[1-(2-benzothiazolylcarbonyl)-5-(methylamino)pentyl]-4-hydroxy-2-pyrrolidinecarboxamide;
N-(Carboxymethyl)-3-cyclohexyl-D-alanyl-N-[(1S)-4-[(aminoiminomethyl)amino]-1-(2-benzothiazolylcarbonyl)butyl]-L-prolinamide;
N-Methyl-D-phenylalanyl-N-[(2S)-[1-(aminoiminomethyl)-3-piperidinyl]-1-(2-benzothiazolylcarbonyl)ethyl]-L-prolinamide;
(S)-N-methyl-D-phenylalanyl-N-[1-[[3-(aminoiminomethyl)phenyl]methyl]-2-(2-benzothiazolyl)-2-oxoethyl]-L-prolinamide;
(2S)-N-[1-[[3-(Aminoiminomethyl)phenyl]methyl]-2-(2-benzothiazolyl)-2-oxoethyl]-1-benzoyl-2-pyrrolidinecarboxamide;
(2S)-N-[4-[(Aminoiminomethyl)amino]-1-(2-benzothiazolylcarbonyl)butyl]-1,2-pyrrolidinedicarboxamide, 1-N,N-dimethylamide;
(2S)-1-Acetyl-N-[4-[(aminoiminomethyl)amino]-1-(2-benzothiazolylcarbonyl)butyl]-3,4-dehydro-2-pyrrolidinecarboxamide; or and pharmaceutically acceptable salts and prodrugs thereof.

7. A pharmaceutical composition comprising a compound of claim 1 and a pharmaceutically acceptable carrier.

8. A pharmaceutical composition made by mixing a compound of claim 1 and a pharmaceutically acceptable carrier.

9. A process for making a pharmaceutical composition comprising mixing a compound of claim 1 and a pharmaceutically acceptable carrier.

10. A method of treating an inflammatory disorder in a subject in need thereof comprising administering to the subject a therapeutically effective amount of a compound of claim 1.

11. The method of claim 10, wherein the inflammatory disorder is an immunomediated inflammatory disorder.

12. The method of claim 11, wherein the immunomediated inflammatory disorder is selected from asthma, allergic rhinitis, rheumatoid arthritis, rheumatoid spondylitis, osteoarthritis, gouty arthritis, arthritic conditions in general, peptic ulcers, ocular and vernal conjunctivitis, inflammatory bowel disease, chronic obstructive pulmonary disease, Crohn's disease, urticaria, bullous pemphigoid, scleroderma, fibrosis, dermatitis, psoriasis, angioedema, eczematous dermatitis, anaphylaxis, hyperproliferative skin disease, inflammatory skin conditions, hepatic cirrhosis, glomerulonephritis, nephritis, vascular inflammation, atherosclerosis or restenosis.

13. The method of claim 11, wherein the immunomediated inflammatory disorder is a mast cell mediated inflammatory disorder.

14. The method of claim 13, wherein the mast cell mediated inflammatory disorder is selected from asthma and allergic rhinitis.

15. The method of claim 14, wherein the mast cell mediated inflammatory disorder is asthma.

16. The method of claim 12, wherein the therapeutically effective amount of the compound is about 0.001 to about 2000 mg/kg/day.

17. The method of claim 16, wherein the therapeutically effective amount of the compound is about 0.001 to about 200 mg/kg/day.

18. The method of claim 15 wherein the compound is administered as an aerosol.

19. The method of claim 15 wherein the compound is administered in combination with a β-adrenergic agonist, a methylxanthine, a cromoglycate or a corticosteroid.

20. The method of claim 19 wherein the β-adrenergic agonist is selected from albuterol, terbutaline, formoterol, fenoterol or prenaline, the methylxanthine is selected from caffeine, theophylline, aminophylline or theobromine, the cromoglycate is selected from cromolyn or nedocromil and the corticosteroid is selected from beclomethasome, triamcinolone, flurisolide, dexamethasone, hydrocortisone or prednisone.

21. The method of claim 10, wherein the compound is administered as a pharmaceutical composition.

22. The method of claim 21 wherein the pharmaceutical composition comprises the compound of Formula I in a pharmaceutically acceptable carrier suitable for topical, oral, suppository, intranasal, inhalation or parenteral administration.

23. A method of treating a disorder mediated by trypsin in a subject in need thereof comprising administering to the subject a therapeutically effective amount of the compound of claim 1.

24. The method of claim 23, wherein the disorder is pancreatitis.

* * * * *